(12) United States Patent
Bordoley et al.

(10) Patent No.: US 9,408,575 B2
(45) Date of Patent: Aug. 9, 2016

(54) EEG KIT

(75) Inventors: Mordechai Bordoley, Wilton, CT (US);
Paul A. Chudy, New York, NY (US);
James G. Donnett, St. Albans (GB);
Ahmet Omurtag, New York, NY (US);
Samah G. Abdel Baki, Brooklyn, NY (US); Andre A. Fenton, New York, NY (US)

(73) Assignee: Bio-Signal Group Corp., Brooklyn, NY (US)

(*) Notice: Subject to any disclaimer, the term of this patent is extended or adjusted under 35 U.S.C. 154(b) by 974 days.

(21) Appl. No.: 13/284,886

(22) Filed: Oct. 29, 2011

(65) Prior Publication Data

US 2012/0143020 A1 Jun. 7, 2012

Related U.S. Application Data

(63) Continuation-in-part of application No. PCT/US2010/001264, filed on Apr. 29, 2010.

(60) Provisional application No. 61/214,880, filed on Apr. 29, 2009, provisional application No. 61/448,430, filed on Mar. 2, 2011.

(51) Int. Cl.
*A61B 5/04* (2006.01)
*A61B 5/00* (2006.01)
*A61B 5/11* (2006.01)

(52) U.S. Cl.
CPC .............. *A61B 5/721* (2013.01); *A61B 5/1114* (2013.01); *A61B 5/6803* (2013.01); *A61B 5/7232* (2013.01);
(Continued)

(58) Field of Classification Search
USPC .................................................. 600/544, 545
See application file for complete search history.

(56) References Cited

U.S. PATENT DOCUMENTS 1,968,767 A * 7/1934 Howard ........................ 224/674
3,942,517 A 3/1976 Bowles
(Continued)

FOREIGN PATENT DOCUMENTS

WO WO-04000115 A1 12/2003
WO WO 04000115 A1 * 12/2003
(Continued)

OTHER PUBLICATIONS

"501(k) Summary (K010460)", Lifelines Ltd., FDA Approval Date: May 14, 2001, 177 pgs.
(Continued)

*Primary Examiner* — Michael Kahelin
*Assistant Examiner* — Tho Tran
(74) *Attorney, Agent, or Firm* — Schwegman Lundberg & Woessner, P.A.

(57) ABSTRACT

An EEG kit can be thought of as "EEG In a Bag" ("EEG-IAB"). The EEG kit can provide a complete, disposable, fast, and easily-used platform to record EEG to measure brain activity. Other physiological information (e.g., oxygen saturation, ECG or EKG, etc.) or other information (e.g., local electrode motion) can also be recorded, such as in time-concordance with the recorded EEG signals. The recorded EEG and other information can be uplinked to a local or remote user interface. A local or remote neurologist can use the EEG information to render a diagnosis in tens of minutes, wherein such information can currently be unavailable, or can require a number of hours to obtain and diagnose. The EEG kit can be very convenient, and can be used in a hospital emergency department (ED), an intensive care unit (ICU), by a first responder, or can be deployed for emergency or disaster preparedness.

24 Claims, 14 Drawing Sheets

(52) U.S. Cl.
CPC ..... *A61B 2505/01* (2013.01); *A61B 2560/0285* (2013.01); *A61B 2560/0431* (2013.01); *A61B 2562/0219* (2013.01); *A61B 2562/046* (2013.01); *A61B 2562/242* (2013.01)

(56) References Cited

U.S. PATENT DOCUMENTS

| | | | |
|---|---|---|---|
| 3,998,213 | A | 12/1976 | Price |
| 4,085,739 | A | 4/1978 | Sams |
| 4,257,424 | A | 3/1981 | Cartmell |
| 4,323,076 | A | 4/1982 | Sams |
| 4,353,372 | A | 10/1982 | Ayer |
| D277,787 | S | 2/1985 | Corbett |
| 4,537,198 | A | 8/1985 | Corbett |
| 4,683,892 | A | 8/1987 | Johansson et al. |
| 4,709,702 | A | 12/1987 | Sherwin |
| 4,967,038 | A | 10/1990 | Gevins et al. |
| 5,119,816 | A | 6/1992 | Gevins |
| 5,222,503 | A | 6/1993 | Ives et al. |
| 5,273,037 | A | 12/1993 | Itil et al. |
| 5,275,172 | A | 1/1994 | Ives |
| 5,293,867 | A | 3/1994 | Oommen |
| 5,357,957 | A | 10/1994 | Itil et al. |
| 5,415,282 | A * | 5/1995 | Kienholz ................ A01N 1/02 206/216 |
| 5,445,162 | A | 8/1995 | Ives |
| 5,479,934 | A | 1/1996 | Imran |
| 5,660,177 | A | 8/1997 | Faupel et al. |
| 5,772,591 | A | 6/1998 | Cram |
| 5,800,351 | A | 9/1998 | Mann |
| 5,813,993 | A | 9/1998 | Kaplan et al. |
| 5,817,029 | A | 10/1998 | Gevins et al. |
| 6,032,064 | A | 2/2000 | Devlin et al. |
| 6,032,065 | A | 2/2000 | Brown |
| 6,067,464 | A | 5/2000 | Musha |
| 6,154,669 | A | 11/2000 | Hunter et al. |
| 6,161,030 | A | 12/2000 | Levendowski et al. |
| 6,175,753 | B1 | 1/2001 | Menkes et al. |
| 6,198,958 | B1 | 3/2001 | Ives et al. |
| 6,201,982 | B1 | 3/2001 | Menkes et al. |
| 6,266,556 | B1 | 7/2001 | Ives et al. |
| 6,289,238 | B1 | 9/2001 | Besson et al. |
| 6,301,493 | B1 | 10/2001 | Marro et al. |
| 6,381,481 | B1 | 4/2002 | Levendowski et al. |
| 6,383,143 | B1 * | 5/2002 | Rost ................ 600/534 |
| 6,394,953 | B1 | 5/2002 | Devlin et al. |
| 6,510,340 | B1 | 1/2003 | Jordan |
| 6,571,123 | B2 | 5/2003 | Ives et al. |
| 6,574,513 | B1 | 6/2003 | Collura et al. |
| 6,577,893 | B1 | 6/2003 | Besson et al. |
| 6,640,122 | B2 | 10/2003 | Manoli et al. |
| 6,654,626 | B2 | 11/2003 | Devlin et al. |
| 6,708,051 | B1 | 3/2004 | Durousseau |
| 7,054,681 | B2 | 5/2006 | Husar et al. |
| 7,551,952 | B2 | 6/2009 | Gevins et al. |
| 7,835,787 | B2 | 11/2010 | Sajda et al. |
| 7,885,706 | B2 | 2/2011 | Ludvig et al. |
| 8,019,402 | B1 | 9/2011 | Kryzpow et al. |
| 8,065,796 | B2 | 11/2011 | Curry |
| 2001/0044573 | A1 * | 11/2001 | Manoli et al. ................ 600/383 |
| 2002/0019588 | A1 | 2/2002 | Marro et al. |
| 2002/0072685 | A1 | 6/2002 | Rymut et al. |
| 2002/0183605 | A1 | 12/2002 | Devlin et al. |
| 2002/0188216 | A1 | 12/2002 | Kayyali |
| 2003/0144600 | A1 | 7/2003 | Yarita |
| 2004/0030258 | A1 * | 2/2004 | Williams ............ A61B 5/0478 600/544 |
| 2005/0054941 | A1 * | 3/2005 | Ting et al. ................ 600/529 |
| 2005/0113666 | A1 | 5/2005 | Bonmassar et al. |
| 2005/0137472 | A1 | 6/2005 | Ryu et al. |
| 2005/0197556 | A1 * | 9/2005 | Stoler ................ 600/383 |
| 2005/0247319 | A1 * | 11/2005 | Berger ................ 128/898 |
| 2005/0277819 | A1 | 12/2005 | Kiani et al. |
| 2006/0161058 | A1 | 7/2006 | Ives et al. |
| 2006/0161072 | A1 | 7/2006 | Mase et al. |
| 2007/0038382 | A1 * | 2/2007 | Keenan ................ 702/19 |
| 2007/0173699 | A1 * | 7/2007 | Mathan et al. ................ 600/300 |
| 2007/0235716 | A1 | 10/2007 | Delic et al. |
| 2007/0238945 | A1 | 10/2007 | Delic et al. |
| 2008/0027345 | A1 | 1/2008 | Kumada et al. |
| 2008/0082019 | A1 * | 4/2008 | Ludving et al. ................ 600/544 |
| 2008/0146958 | A1 * | 6/2008 | Guillory ............ A61B 5/0476 600/544 |
| 2008/0226255 | A1 * | 9/2008 | Estes ................ 386/66 |
| 2008/0306397 | A1 | 12/2008 | Bonmassar et al. |
| 2009/0105576 | A1 | 4/2009 | Do et al. |
| 2009/0105577 | A1 | 4/2009 | Wu et al. |
| 2009/0281446 | A2 | 11/2009 | Ludvig et al. |
| 2009/0326404 | A1 | 12/2009 | Sajda et al. |
| 2010/0036275 | A1 | 2/2010 | Alkire |
| 2010/0041962 | A1 | 2/2010 | Causevic et al. |
| 2010/0274152 | A1 | 10/2010 | McPeck et al. |
| 2011/0004089 | A1 | 1/2011 | Chou |
| 2011/0015503 | A1 | 1/2011 | Joffe et al. |
| 2011/0144522 | A1 | 6/2011 | Sajda et al. |
| 2011/0270117 | A1 | 11/2011 | Warwick et al. |
| 2011/0282231 | A1 | 11/2011 | Pradeep et al. |
| 2015/0011857 | A1 | 1/2015 | Henson et al. |

FOREIGN PATENT DOCUMENTS

| | | |
|---|---|---|
| WO | WO-2008109694 A1 | 9/2008 |
| WO | WO-2010129026 A2 | 11/2010 |
| WO | WO-2010129026 A3 | 2/2011 |
| WO | WO-2013126798 A2 | 8/2013 |
| WO | WO-2013126798 A3 | 8/2013 |

OTHER PUBLICATIONS

"501(k) Summary (K042039)", Cleveland Medical Devices, Inc., FDA Approval Date: Nov. 17, 2004, 170 pgs.

"Electro-Cap International, Inc.", http://www.electro-cap.com/caps.htm, [website visited Apr. 28, 2010], 2 pgs.

"HydroCel Geodesic Sensor Nets", http://www.egi.com/research-division-research-products/sensor-nets, [website visited Apr. 28, 2010], 2 pgs.

"International Application Serial No. PCT/US2010/001264, Internationl Preliminary Report on Patentability mailed Aug. 24, 2011", 19 pg.

"International Application Serial No. PCT/US2010/001264, Invitation to Pay Additional Fee mailed Aug. 17, 2010", 7 pgs.

"International Application Serial No. PCT/US2010/001264, Search Report mailed Dec. 13, 2010", 17.

"International Application Serial No. PCT/US2010/001264, Written Opinion mailed Dec. 13, 2010", 17.

Fenton, A. A., et al., "A Step Toward Routine EEG Recording in the Emergency Department", BioSignal, poster presentation, (Dec. 6, 2009), 1 pg.

Omurtag, Ahmet, et al., "BioSignal Grant Application", grant application submission date was Sep. 1, 2009, but it is unclear whether this has ever published or whether the submission was Non-Confidential, 138 pgs.

"International Application Serial No. PCT/US2013/027464, International Preliminary Report on Patentability mailed Sep. 4, 2014", 13 pgs.

"International Application Serial No. PCT/US2013/027464, International Search Report mailed Oct. 7, 2013", 6 pgs.

"International Application Serial No. PCT/US2013/027464, Invitation to Pay Additional Fees and Partial Search Report mailed Jun. 18, 2013", 7 pgs.

"International Application Serial No. PCT/US2013/027464, Written Opinion mailed Oct. 7, 2013", 11 pgs.

* cited by examiner

EEG KIT

CLAIM OF PRIORITY

1. This application is a continuation-in-part, under 35 U.S.C. §111(a) of International Application No. PCT/US2010/001264, which was filed on Apr. 29, 2010 and which published as WO 2010/129026 on Nov. 11, 2010, and which claimed the benefit of priority under 35 U.S.C. §119(e) to U.S. Provisional Patent Application No. 61/214,880, entitled "EEG KIT," which was filed on Apr. 29, 2009, each of which is incorporated herein by reference in its entirety, and the benefit of priority of each of which is hereby presently claimed in this present patent application.

2. This application also claims priority under 35 U.S.C. §119(e) to U.S. Provisional Patent Application Ser. No. 61/448,430, which was filed on Mar. 2, 2011, which application is hereby incorporated by reference herein in its entirety.

CROSS-REFERENCE TO RELATED PATENT DOCUMENTS

This patent application is related to James G. Donnett et al. U.S. patent application Ser. No. 11/694,816, entitled BRAIN SIGNAL TELEMETRY AND SEIZURE PREDICTION, filed on Mar. 30, 2007, which is hereby incorporated herein by reference in its entirety.

This patent application is related to James G. Donnett et al. U.S. patent application Ser. No. 11/694,855, entitled SEIZURE PREDICTION USING BRAIN SIGNAL TELEMETRY, filed on Mar. 30, 2007, which is hereby incorporated herein by reference in its entirety.

STATEMENT REGARDING FEDERALLY SPONSORED RESEARCH OR DEVELOPMENT

This invention was made with government support under awards numbered U44 NS057951-01 and RC3NS070658-01 from the National Institute of Neurological Disorders and Stroke. The government has certain rights in this invention.

COPYRIGHT NOTICE

A portion of the disclosure of this patent document contains material that is subject to copyright protection. The copyright owner has no objection to the facsimile reproduction by anyone of the patent document or the patent disclosure, as it appears in the Patent and Trademark Office patent files or records, but otherwise reserves all copyright rights whatsoever. The following notice applies to the software and data as described below and in the drawings that form a part of this document: Copyright 2009, Bio-Signal Group Corp., All Rights Reserved.

TECHNICAL FIELD

This document pertains generally to medical diagnostic devices and methods, and more particularly, but not by way of limitation, to an electroencephalographic (EEG) kit and user interfaces and methods for use in conjunction therewith.

BACKGROUND

Electroencephalography (EEG) refers to recording of the electrical activity of the brain over time. Such electrical activity can be produced by bioelectric events within the brain. EEG information can be used to diagnose brain status, such as epilepsy, however, obtaining it can involve cumbersome attachment of over twenty tethered electrodes by a trained technician.

OVERVIEW

This document describes an EEG kit, which can be thought of as "EEG In a Bag" ("EEG-IAB"). The EEG kit can provide a complete, disposable, fast, and easy to use platform to record EEG to measure brain activity. The recorded EEG information can be uplinked to a local or remote user interface. A local or remote neurologist can use the EEG information to render a diagnosis in tens of minutes, wherein such information can currently be unavailable, or can require a number of hours to obtain and diagnose. The EEG kit can be very convenient. In certain examples, the EEG kit can be used in a hospital emergency department (ED), an intensive care unit (ICU), by a first responder, at home, in a battlefield, or can be deployed for emergency or disaster preparedness.

In an emergency department, for example, it is estimated that 14 million (or about 10%) of all emergency department visits annually in the U.S. involve altered mental status (AMS). When a patient with altered mental status arrives at the emergency department, one immediate concern is to determine whether the patient is currently exhibiting seizure activity, or exhibiting symmetry of electrical brain activity which can indicate brain dysfunction, for example following a traumatic injury. One in ten children visiting the emergency department have febrile seizures, which are non-convulsive, and thus not apparent. One in 500 children visiting the emergency department will develop severe epilepsy. In such cases, undiagnosed seizures can cause brain damage, leading to further seizures. The EEG-IAB kit described herein can conveniently be used to quickly confirm or eliminate the presence of seizure activity, so that treatment can be quickly adjusted accordingly.

Currently, EEG recording in the emergency department can be difficult. As a result, it is an under-used diagnostic tool in the emergency department setting. Few emergency departments are equipped with EEG recording devices and have a knowledgeable technician available to hook up and operate such EEG recording devices. Even when an EEG recording device is available, attaching head electrodes for EEG recording can be a 30 minute to 45 minute procedure. Moreover, the tethered bundle of wiring leading from the head electrodes to the EEG recording device can effectively act as an antenna—picking up electrical noise, such as from other nearby equipment, which can interfere with the EEG recording interpretations. Furthermore, the tethered bundle of wiring can also constrain much needed flexibility and often desirable patient mobility. This can be a problem in the dynamic environment of the emergency department (ED), in which saving time can be crucial to patient outcome and, at the very least, can impact cost of the services rendered. EEG recording solutions designed for an epilepsy monitoring unit (EMU) can be particularly vulnerable to the much higher levels of 60 Hz and other ambient noise present in the emergency department. The EMU can shield or isolate the EEG recording from other AC-powered electrical equipment. The emergency department cannot. Thus, an EEG recording solution designed for the EMU can be impaired or ineffective in the ED.

The EEG-IAB kit described herein can address some or all of the above concerns, and can help increase the quality and timeliness of care, and can significantly lower the cost. The EEG-IAB kit described herein can help curb health care costs, such as by helping provide low cost diagnostics and increased outpatient care. The EEG-IAB kit described herein can help leverage the efficiencies of telemedicine and digital electronic medical records (EMR). The EEG-IAB kit described herein can also help address the country's dramatic increases in emergency department visits. From a commercial perspective, the EEG-IAB kit described herein can use a fee for service model, which can provide value in the form of an ongoing diagnostic service.

Example 1 can include subject matter that can include an apparatus comprising an electroencephalographic (EEG) monitoring kit comprising a kit package. The kit package can comprise an EEG recording module, which can be configured to be worn on a head of a patient. The EEG recording module can comprise a memory that can be configured for recording a plurality of EEG signals from the patient. The kit package can comprise a cap or other headpiece, which can be sized and shaped to be worn on the head of the patient. The headpiece can comprise a plurality of non-surgically implanted scalp-wearable electrode assemblies that can be configured to be electrically connected to the EEG recording module. The kit package can comprise an electrical connector cable. The cable can have a length that is less than 50 centimeters. The cable can be configured to couple the EEG recording module to the headpiece, such as when both are worn on the head of the patient, such as to communicate the EEG signals from the electrode assemblies to the EEG recording module. The kit package can comprise a fluid-impervious single-use cover, which can be configured to be directly or indirectly mounted to the headpiece or to the head of the patient. The cover can be sized or shaped or otherwise configured to carry the EEG recording module within the cover and can be configured to permit the cable to extend out from the cover to the headpiece.

In Example 2, the subject matter of Example 1 can optionally be configured such that the cover comprises a pouch comprising an adhesive seal, which can be configured to seal the EEG recording module within the pouch with the cable extending out from the pouch.

In Example 3, the subject matter of any one or more of Examples 1-2 can optionally be configured such that opening the sealed pouch to remove the EEG recording module from the pouch renders the pouch unsuitable for subsequent use with the EEG recording module.

In Example 4, the subject matter of any one or more of Examples 1-3 can optionally be configured such that the cover comprises a pouch that comprises a mount, which can be configured to directly or indirectly mount the pouch to the headpiece or the head of the patient.

In Example 5, the subject matter of any one or more of Examples 1-4 can optionally be configured such that the EEG kit package can comprise a headband, which can be sized or shaped or otherwise configured to be worn directly or indirectly about the head of the patient. The pouch can comprise the mount including a sleeve that can be sized or shaped or otherwise configured to pass the headband through the sleeve such as for mounting the pouch such as for being worn directly or indirectly about the head of the patient.

In Example 6, the subject matter of any one or more of Examples 1-5 can optionally be configured such that the headband can include (or even be entirely comprised of) an elastic portion, such as to allow stretching of the headband.

In Example 7, the subject matter of any one or more of Examples 1-6 can optionally be configured such that the headband can further include an additional length adjustment feature, e.g., other than or beyond the stretching.

In Example 8, the subject matter of any one or more of Examples 1-7 can optionally be configured such that the additional length adjustment feature can include a series of spaced-apart affixation tabs located on the headband.

In Example 9, the subject matter of any one or more of Examples 1-8 can optionally be configured such that the headpiece can comprise a head-receiving configuration of support members. The configuration of support members can carry a plurality of electrode assemblies that can be electrically connected to the EEG recording module and that can respectively ride along a respective position adjustment track or other position adjustment means, for example, so as to be capable of being individually relocated by a user from a first location on the patient's head to a different second location on the patient's head while the headpiece is in place on the patient's head.

In Example 10, the subject matter of any one or more of Examples 1-9 can optionally be configured such that at least one of the electrode assemblies comprises a plunger, which can be configured to allow user-adjustment of an electrode toward a scalp of the patient. The plunger can be configured to rupture a seal such as to allow user-actuated release of an at least somewhat flowable conductive substance toward a skin-electrode interface such as to assist in obtaining good electrical conduction at the skin-electrode interface.

In Example 11, the subject matter of any one or more of Examples 1-10 can optionally be configured such that each one of the electrode assemblies can comprise a respective accelerometer attached to that one of the electrode assemblies and wherein the EEG recording module can further comprise a signal processor circuit coupled to the accelerometers. The signal processor can be configured to permit detecting relative movement of that particular one of the electrode assemblies beyond global motion of the patient's head or body.

In Example 12, the subject matter of any one or more of Examples 1-11 can optionally be configured such that the EEG recording module can comprise an impedance test circuit, which can be configured to measure a skin-electrode impedance of an individual electrode configured to provide an EEG signal.

In Example 13, the subject matter of any one or more of Examples 1-12 can optionally comprise a user interface, which can be configured to be capable of being communicatively coupled to the memory of the EEG recording module and configured to receive information from the recorded plurality of EEG signals, and wherein the user interface includes or is configured to be coupled to a camera to obtain images of the patient to be stored in concordance with the plurality of EEG signals.

In Example 14, the subject matter of any one or more of Examples 1-13 can optionally comprise the EEG recording module including a non-EEG physiological sensor interface that can be configured to receive at least one non-EEG physiological signal. The EEG recording module can be configured to record the non-EEG physiological signal in concordance with one or more of the plurality of EEG signals.

In Example 15, the subject matter of any one or more of Examples 1-14 can optionally comprise the headpiece including a local position monitor that can be configured to monitor the position of at least one of the electrode assemblies and to provide an indication of the position of the monitored at least one electrode assembly to the memory of the EEG recording module for recording.

In Example 16, the subject matter of any one or more of Examples 1-15 can optionally comprise an adjunct computing device, which can be capable of being communicatively coupled to the memory of the EEG recording module and can be configured to receive information from the recorded plurality of EEG signals. The adjunct computing device can include or can be configured to be coupled to processor, which can be configured to perform seizure detection using information from the recorded plurality of EEG signals.

In Example 17, the subject matter of any one or more of Examples 1-16 can optionally be configured such that the adjunct computing device can be configured to be communicatively coupled to a plurality of EEG recording modules.

In Example 18, the subject matter of any one or more of Examples 1-17 can optionally be configured such that the adjunct computing device can include or can be coupled to a memory circuit that can include instructions that, when performed by a processor circuit of the adjunct computing device, can analyze EEG signals from the plurality of EEG recording modules associated with different patients such as to prioritize patients for further attention.

In Example 19, the subject matter of any one or more of Examples 1-18 can optionally be configured such that the adjunct computing device can include or can be coupled to a memory circuit that can be configured to record a measure of performance of a plurality of human reviewers.

Example 20 can comprise, or can optionally be combined with the subject matter of any one or more of Examples 1-19, to comprise an apparatus comprising an electroencephalographic (EEG) monitoring kit comprising a kit package. The kit package can comprise an EEG recording module, which can be configured to be worn on a head (or other body portion) of a patient. The EEG recording module can comprise a memory that can be configured for recording a plurality of EEG signals from the patient. The kit package can comprise a headpiece, which can be sized and shaped to be worn on the head of the patient. The headpiece can comprise a plurality of non-surgically implanted scalp-wearable electrode assemblies that can be configured to be electrically connected to the EEG recording module. The kit package can comprise an electrical connector cable. The cable can have a length that is less than 50 centimeters. The cable can be configured to couple the EEG recording module to the headpiece, such as when both are worn on the head of the patient, such as to communicate the EEG signals from the electrode assemblies to the EEG recording module. The kit package can include a fluid-impervious single-use cover. The cover can be configured to be directly or indirectly mounted to the headpiece or to the head (or other body part) of the patient. The cover can be sized or shaped or otherwise configured to carry the EEG recording module within the cover and configured to permit the cable to extend out from the cover to the headpiece. The cover can comprise a pouch that can comprise an adhesive seal, which can be configured to seal the EEG recording module within the pouch such as with the cable extending out from the pouch. The pouch can be configured such that opening the sealed pouch to remove the EEG recording module from the pouch renders the pouch unsuitable for subsequent use with the EEG recording module. The pouch can comprise a mounting sleeve, which can be configured to directly or indirectly mount the pouch to the headpiece or the head of the patient. The kit package can comprise a headband, which can including a stretchable elastic portion, the headband sized or shaped or otherwise configured to be worn directly or indirectly about the head of the patient, and wherein the mounting sleeve of the pouch is sized or shaped or otherwise configured to pass the headband through the sleeve for mounting the pouch for being worn directly or indirectly about the head of the patient.

In Example 21, the subject matter of any one or more of Examples 1-20 can optionally be configured such that each one of the electrode assemblies comprises a respective accelerometer attached to that one of the electrode assemblies. The EEG recording module can further comprise a signal processor circuit that can be coupled to one or more of the accelerometers. The signal processor can be configured to permit detecting relative movement of that particular one of the electrode assemblies beyond global motion of the patient's head or body. The EEG recording module can comprise an impedance test circuit, which can be configured to measure a skin-electrode impedance of an individual electrode configured to provide an EEG signal.

Example 22 can comprise, or can optionally be combined with the subject matter of any one or more of Examples 1-21 to comprise, one or more of inserting an EEG recording module into a fluid-impervious single-use cover (which can be configured to be directly or indirectly mounted to a headpiece or to a head of the patient, the cover sized or shaped or otherwise configured to carry the EEG recording module within the cover and which can be configured to permit a cable to extend out from the cover to the headpiece) and sealing the cover in a manner such that opening the cover to remove the EEG recording module renders the cover unsuitable for re-use.

Further, the subject matter of one or more of the above Examples can be used in any permutation or combination with the subject matter one or any combination of the below-described Examples A1-A29, Examples B1-B29, Examples C1-C17

In Example A1, an apparatus can comprise: an ambulatory intrinsic brain signal processor circuit, which can be configured to be coupled to a plurality of electrodes. The signal processor circuit can comprise: a digital multiplexer circuit, which can be configured to be coupled to the electrodes, and which can be configured to multiplex brain signal data from different electrodes together such as into a multiplexed data stream; an ambulatory transceiver circuit, which can be configured to wirelessly communicate information to a remote transceiver, and which can be configured to wirelessly receive user-programming information from the remote transceiver; and a controller circuit, which can be configured to permit a user to control: which of the electrodes contribute data to the multiplexed data stream; a data resolution of the electrodes that contribute data to the multiplexed data stream; and whether data contributed by a particular electrode includes a user-selected one of at least one of: (1) neural action potential data, from which neural field potential data has been reduced or removed; (2) neural field potential data, from which neural action potential data has been reduced or removed; and (3) both neural action potential and neural field potential data.

In Example A2, the apparatus of Example A1, can optionally further comprise a plurality of electrode assemblies, each electrode assembly can include: at least one electrode, which can be configured to be coupled to a brain of a subject; a brain signal sense amplifier circuit, which can be coupled to the electrode, and which can be configured to sense an intrinsic brain signal and to output a resulting sensed brain signal that is indicative of the intrinsic brain signal; a filter circuit, which can be coupled to the sense amplifier circuit, the filter circuit that can include a user-programmable frequency filtering characteristic that can be configured to allow a user to select between at least two of: (1) passing neural action potential frequencies; (2) passing neural field potential frequencies; and (3) passing both neural action potential and neural field potential frequencies; and an analog-to-digital converter ("ADC") circuit, which can be coupled to the filter circuit, the ADC can be configured to digitize brain signal information passed by the filter circuit, the digitizing occurring in close proximity to the electrode.

In Example A3, the apparatus of one or any combination of Examples A1-A2 can optionally further include a sense amplifier circuit that can be configured to include: a first input, which can be configured to be coupled to a first signal sensing electrode that can be configured for sensing a localized neural action potential signal; a second input, which can be configured to be coupled to a reference signal sensing electrode that can be configured for sensing a neural field potential signal; and wherein the amplifier can be configured to reduce or remove a common-mode neural field potential signal present between the reference signal sensing electrode and the first signal sensing electrode, and to output a resulting differential signal indicative of a neural action potential.

In Example A4, the apparatus of one or any combination of Examples A1-A3 can optionally further include a sense amplifier circuit that can comprise a user-programmable gain.

In Example A5, the apparatus of one or any combination of Examples A1-A4 can optionally include a sense amplifier with a user-programmable gain that can include a neural action potential setting and a neural field potential setting, wherein the neural action potential setting and the neural field potential setting can provide different gain values.

In Example A6, the apparatus of one or any combination of Examples A1-A5 can optionally include an ADC that can comprise a sampling rate and sampling resolution that are both user-programmable.

In Example A7, the apparatus of one or any combination of Examples A1-A6 can optionally be configured such that at least one of the sampling rate and the sampling resolution can include a neural action potential setting and a neural field potential setting, wherein the neural action potential setting and the neural field potential setting can provide at least one of different sampling rate values and different sampling resolution values.

In Example A8, the apparatus of one or any combination of Examples A1-A7 can optionally include an ambulatory memory device, which can be configured to store brain signal information.

In Example A9, the apparatus of one or any combination of Examples A1-A8 optionally can be configured to provide user control over whether a particular electrode's data contribution to the multiplexed data stream is at least one of: provided to the transmitter for communication to remote receiver or provided to the ambulatory memory device for storage.

In Example A10, the apparatus of one or any combination of Examples A1-A9 can optionally include a physiological event detector, communicatively coupled to the controller circuit to trigger at least one of storage or communication of brain signal information in response to detecting a specified physiological event.

In Example A11, the apparatus of one or any combination of Examples A1-A10 optionally can be configured to include a physiological event detector that comprises at least one of: (1) a heart rate detector; (2) a neural field potential pattern detector; and (3) a neural action potential pattern detector.

In Example A12, the apparatus of one or any combination of Examples A1-A11 optionally can be configured to include a remote user interface comprising: the remote transceiver; a digital demultiplexer circuit, which can be coupled to the remote transceiver; and a user interface controller circuit, which can be coupled to the digital demultiplexer circuit and the remote transceiver, the user interface controller circuit can be configured to receive a user instruction.

In Example A13, the apparatus of one or any combination of Examples A1-A12 optionally can be configured to include a remote user interface that can include at least one of: (1) a digital recorder circuit; and (2) a digital-to-analog converter (DAC) circuit and an analog recorder circuit.

In Example A14, the apparatus of one or any combination of Examples A1-A13 optionally can be configured to include a Normal template, which can provide an indication of correlation of the brain potentials during at least one non-seizure time period of the subject, wherein the non-seizure time period can exclude a time period during a seizure, and wherein the non-seizure time period can exclude at least a first specified time period preceding the seizure; a Non-Normal template, providing an indication of correlation of the brain potentials during at least one pre-seizure time period or seizure time period of the subject, wherein the pre-seizure time period can be less or equal to a second specified time period before the seizure, and wherein the seizure occurs during the seizure time period; a monitoring circuit, which can be configured to form, during a sampling time period, an indication of correlation of the brain potentials using the at least two different locations of a brain of the subject; and an upcoming seizure prediction circuit, which can be configured to predict an upcoming seizure such as at least in part by comparing the indication of correlation obtained during the sampling time period to each of the Normal and Non-Normal templates.

In this document, the correlation can include a quantitative indication of correlation of the brain potentials arising at different electrode locations or of different brain potentials arising at the same electrode locations (e.g., such as a 7 Hz theta oscillation and a 40 Hz gamma oscillation, or any other pair of brain signals that may co-occur). In an example, the correlation may be computed as the Pearson, Spearman, or Kendall correlation or one or more other measurements of correlation or covariance, such as a product moment. In an example, the correlation may itself comprise a set of correlations, such as a vector of correlations where an individual element of the vector represents the relationship between two (or more) brain potential signals arising at different electrodes sites or from the same electrode site, or from any combination of signals from the same and different electrode sites. The Normal or one or more other templates can include or provide a quantitative indication of correlation, as discussed above.

In Example A15, the apparatus of one or any combination of Examples A1-A14 can optionally include a data integrity circuit, which can be communicatively coupled to receive data contributed by a particular electrode, and which can be configured to determine whether data contributed by a particular electrode includes a valid or useful information about an intrinsic neural signal.

In Example A16, the apparatus of one or any combination of Examples A1-A15 can optionally include a data compression circuit, which can be communicatively coupled to receive data contributed by a particular electrode, and which can be configured to extract parameterized information about a neural event and a corresponding time.

Example A11 can include an apparatus that can comprise: a plurality of electrode assemblies. Each electrode assembly can include: at least one electrode, which can be configured to be coupled to a brain of a subject; a brain signal sense amplifier circuit, which can be coupled to the electrode, and which can be configured to sense an intrinsic brain signal and to output a resulting sensed brain signal that is indicative of the intrinsic brain signal; a filter circuit, which can be coupled to the sense amplifier circuit, the filter circuit can include a user-programmable frequency filtering characteristic that can be configured to allow a user to select between at least two of: (1) passing neural action potential frequencies; (2) passing neural field potential frequencies; and (3) passing both neural action potential and neural field potential frequencies; an analog-to-digital converter ("ADC") circuit, coupled to the filter circuit, the ADC circuit can be configured to digitize brain signal information passed by the filter circuit, the digitizing occurring in close proximity to the electrode; an ambulatory memory device, which can be configured to store brain signal information; an ambulatory signal processor circuit, which can be coupled to the electrode assemblies. The signal processor circuit can include: a digital multiplexer circuit, which can be coupled to the electrode assemblies, and which can be configured to multiplex data from different electrode assemblies together into a multiplexed data stream; a transceiver circuit, which can be configured to communicate information to a remote transceiver; and a controller circuit. The controller can be configured to control the digital multiplexer to permit a user to control: which electrodes contribute data to the multiplexed data stream; a data resolution of each electrode contributing data to the multiplexed data stream; whether a particular electrode's data contribution to the multiplexed data stream is at least one of: provided to the transmitter for communication to the remote receiver or provided to the ambulatory memory device for storage; and whether data contributed by a particular electrode includes a user-selected one of: (1) neural action potential data, from which neural field potential data has been reduced or removed; (2) neural field potential data, from which neural action potential data has been reduced or removed; and (3) both neural action potential and neural field potential data.

Example A18 can include an apparatus that can comprise: ambulatory means for acquiring brain signals at different locations of a subject's brain; and ambulatory means for receiving information from user input to control: which locations contribute data to a monitored data stream; a data resolution of the locations that contribute data to the monitored data stream; and whether data contributed by a particular location includes a user-selected one of: (1) neural action potential data, from which neural field potential data has been reduced or removed; (2) neural field potential data, from which neural action potential data has been reduced or removed; and (3) both neural action potential and neural field potential data.

Example A19 can include a method that can comprise: acquiring brain signals at different locations of an ambulatory subject's brain; receiving, at the ambulatory subject, information from user input to control: which locations contribute data to a monitored data stream; a data resolution of the locations that contribute data to the monitored data stream; and whether data contributed by a particular location includes a user-selected one of: (1) neural action potential data, from which neural field potential data has been reduced or removed; (2) neural field potential data, from which neural action potential data has been reduced or removed; and (3) both neural action potential and neural field potential data.

In Example A20, the method of Example A19 can optionally comprise performing, at an assembly carrying an electrode, the acts of sensing an intrinsic brain signal to provide a resulting sensed brain signal that is indicative of the intrinsic brain signal; filtering the sensed brain signal, including configuring a filter characteristic by using user input to select between at least two of: (1) passing neural action potential frequencies; (2) passing neural field potential frequencies; and (3) passing both neural action potential and neural field potential frequencies; and digitizing the filtered sensed brain signal.

In Example A21, the method of one or any combination of Examples A19-A20 can optionally include sensing a first intrinsic brain signal with respect to a reference signal; sensing a second intrinsic brain signal with respect to the reference signal; and combining the first and second intrinsic brain signals into a differential signal such as indicative of a difference between the first and second intrinsic brain signals and reducing or removing a common mode signal represented by the reference signal.

In Example A22, the method of one or any combination of Examples A19-A21 can optionally include providing, at the subject, a user-programmable gain that can include a neural action potential setting and a neural field potential setting, wherein the neural action potential setting and the neural field potential setting can provide different gain values.

In Example A23, the method of one or any combination of Examples A19-A22 can optionally include providing, at the subject, at least one of a user-programmable sampling rate and a user-programmable sampling resolution, wherein at least one of the user-programmable sampling rate and the user-programmable sampling resolution can include a neural action potential setting and a neural field potential setting, wherein the neural action potential setting and the neural field potential setting can provide at least one of different sampling rate values and different sampling resolution values.

In Example A24, the method of one or any combination of Examples A19-A23 can optionally include storing, at the subject, brain signal information, including providing user control over whether a particular electrode's data contribution to the monitored data stream is at least one of: provided to the transmitter for communication to the remote receiver or stored at the subject.

In Example A25, the method of one or any combination of Examples A19-A24 can optionally include detecting a physiological event of the subject; and triggering at least one of storage and communication of brain signal information in response to detecting the physiological event.

In Example A26, the method of one or any combination of Examples A19-A25 can optionally include detecting the physiological event comprising at least one of: detecting a heart rate; detecting a specified neural field potential pattern; and detecting a specified neural action potential pattern.

In Example A27, the method of one or any combination of Examples A19-A26 can optionally include: receiving a Normal template providing an indication of correlation of intrinsic brain potentials during at least one non-seizure time period of a subject, wherein the non-seizure time period can exclude a seizure time period of a seizure, and wherein the non-seizure time period can exclude at least a first specified time period preceding the seizure; receiving a Non-Normal template providing an indication of correlation of the brain potentials during at least one pre-seizure time period or seizure time period of the subject, wherein the pre-seizure time period can be less or equal to a second specified time period before the seizure, and wherein the seizure occurs during the seizure time period; monitoring intrinsic brain potentials using at least two different locations of a brain of the subject and forming an indication of correlation of the brain potentials at the at least two different locations during a sampling time period; and predicting an upcoming seizure at least in part by comparing the indication of correlation of the brain potentials obtained during the sampling time period to each of the Normal and Non-Normal templates.

In Example A28, the method of one or any combination of Examples A19-A27 can optionally comprise determining whether data contributed by a particular location includes a valid or useful information about an intrinsic neural signal.

In Example A29, the method of one or any combination of Examples A19-A29 can optionally comprise extracting, from data contributed by a particular location, parameterized information about a neural event and a corresponding time.

Example B1 can include a method that can comprise: receiving a Normal template that can provide an indication of correlation of intrinsic brain potentials during at least one non-seizure time period of a subject, wherein the non-seizure time period can exclude a seizure time period of a seizure, and wherein the non-seizure time period can exclude at least a first specified time period preceding the seizure; receiving a Non-Normal template that can provide an indication of correlation of the brain potentials during at least one pre-seizure time period or seizure time period of the subject, wherein the pre-seizure time period can be less than or equal to a second specified time period before the seizure, and wherein the seizure occurs during the seizure time period; monitoring intrinsic brain potentials using at least two different locations of a brain of the subject and forming an indication of correlation of the brain potentials at the at least two different locations during a sampling time period; and predicting an upcoming seizure at least in part by comparing the indication of correlation of the brain potentials obtained during the sampling time period to each of the Normal and Non-Normal templates.

In Example B2, the method of Example B1 can optionally comprise: receiving a seizure occurrence input to establish a time of at least one known seizure of a subject; monitoring brain potentials using at least two different locations of the brain of the subject; and forming the Normal and Non-Normal templates using information from the monitoring and the time of the at least one known seizure of the subject.

In Example B3, the method of one or any combination of Examples B1-B2 can optionally be performed such that the intrinsic brain potentials can include local field potentials.

In Example B4, the method of one or any combination of Examples B1-B3 can optionally be performed such that the intrinsic brain potentials can include intrinsic neuronal action potentials.

In Example B5, the method of one or any combination of Examples B1-B4 can optionally be performed such that the monitoring intrinsic brain potentials can comprise: acquiring and digitizing neuronal action potential signals at separate locations of different electrodes; communicating information about the digitized action potential signals to an ambulatory transmitter circuit located at the subject; and transmitting information about the digitized action potential signals to at least one of a local or remote user-interface device.

In Example B6, the method of one or any combination of Examples B1-B5 can optionally be performed such that the monitoring intrinsic brain potentials can comprise monitoring single-unit activity (SUA) of individual neurons.

In Example B7, the method of one or any combination of Examples B1-B6 can optionally be performed such that the monitoring intrinsic brain potentials can comprise monitoring multi-unit activity (MUA) of a set of nearby individual neurons.

In Example B8, the method of one or any combination of Examples B1-B7 can optionally be performed such that the monitoring can include counting a number of neuronal signal energy indications that exceed a specified threshold value.

In Example B9, the method of one or any combination of Examples B1-B8 can optionally comprise monitoring that includes integrating a neuronal signal over time.

In Example B10, the method of one or any combination of Examples B1-B9 can optionally comprise a first specified time period that is at least one hour.

In Example B11, the method of one or any combination of Examples B1-B10 can optionally comprise a second specified time period that is less than or equal to one hour.

In Example B12, the method of one or any combination of Examples B1-B11 can optionally comprise at least one of the first and second specified time periods being user-programmable for a particular subject.

In Example B13, the method of one or any combination of Examples B1-B12 optionally can comprise at least one of the Normal template, the Non-Normal template, and the forming of the indication of correlation during a sampling time period can include measuring a covariance of an brain potential indication using at least two different locations of a brain of the subject.

In Example B14, the method of one or any combination of Examples B1-B13 can optionally comprise predicting an upcoming seizure, which can include: providing a greater likelihood of the upcoming seizure when the indication of correlation obtained during the seizure prediction time becomes less closely matched to the indication of correlation of the Normal template and becomes more closely matched to the indication of correlation of the Non-Normal template; and providing an alert when the likelihood of the upcoming seizure exceeds a specified alert threshold value.

In Example B15, the method of one or any combination of Examples B1-14 can optionally comprise receiving a Non-Normal template, which can comprise receiving a Pre-Seizure template providing an indication of correlation of the brain potentials during at least one pre-seizure time period of the subject, wherein the pre-seizure time period can be less or equal to a second specified time period before the seizure.

Example B16 can include an apparatus that can comprising: means for providing a Normal template providing an indication of correlation of intrinsic brain potentials during at least one non-seizure time period of a subject, wherein the non-seizure time period can exclude a seizure time period of a seizure, and wherein the non-seizure time period can exclude at least a first specified time period preceding the seizure; means for providing a Non-Normal template providing an indication of correlation of the brain potentials during at least one pre-seizure time period or seizure time period of the subject, wherein the pre-seizure time period can be less or equal to a second specified time period before the seizure, and wherein the seizure occurs during the seizure time period; means for monitoring intrinsic brain potentials using at least two different locations of a brain of the subject and forming an indication of correlation of the brain potentials at the at least two different locations during a sampling time period; and means for predicting an upcoming seizure such as at least in part by comparing the indication of correlation of the brain potentials obtained during the sampling time period to each of the Normal and Non-Normal templates.

In Example B17, the apparatus of Example B16 can optionally be configured such that the means for the monitoring brain potentials can comprise: separate electrodes, each electrode can include an integrated sensing circuit and an integrated digitizing circuit located at that electrode; and an ambulatory transmitter circuit located at the subject, the transmitter circuit can be communicatively coupled to the electrodes, the transmitter can be configured for wireless data transmission to a local or remote external receiver.

In Example B18, the apparatus of one or any combination of Examples B16-B17 can optionally be configured such that the means for predicting an upcoming seizure using a comparing of the indication of correlation obtained during the sampling time period to each of the Normal and Non-Normal templates can comprise: a seizure likelihood indicator that can be configured to provide a greater likelihood of the upcoming seizure when the indication of correlation obtained during the seizure prediction time becomes less closely matched to the indication of correlation of the Normal template and more closely matched to the indication of correlation of the Non-Normal template; and an alert comparator circuit, which can be coupled to the seizure likelihood indicator, the alert comparator circuit can be configured to provide an alert when the likelihood of the upcoming seizure exceeds a specified alert threshold value.

Example B19 can include an apparatus that can comprise: an intrinsic brain potentials monitor circuit, which can be configured to monitor brain potentials such as using at least two different locations of a brain of the subject; and a neuronal signal processor circuit, which can comprise: a Normal template, which can provide an indication of correlation of the brain potentials during at least one non-seizure time period of the subject, wherein the non-seizure time period can exclude a time period during a seizure, and wherein the non-seizure time period can exclude at least a first specified time period preceding the seizure; a Non-Normal template, which can provide an indication of correlation of the brain potentials during at least one pre-seizure time period or seizure time period of the subject, wherein the pre-seizure time period can be less or equal to a second specified time period before the seizure, and wherein the seizure occurs during the seizure time period; a monitoring circuit, which can be configured to form, during a sampling time period, an indication of correlation of the brain potentials using the at least two different locations of a brain of the subject; and an upcoming seizure prediction circuit, which can be configured to predict an upcoming seizure at least in part by comparing the indication of correlation obtained during the sampling time period to each of the Normal and Non-Normal templates.

In Example B20, the apparatus of Example B19 can optionally comprise a seizure occurrence input, which can be configured to receive information to establish a time of at least one known seizure of a subject for use in forming at least one of the Normal template and the Non-Normal template.

In Example B21, the apparatus of one or any combination of Examples B19-B20 can optionally be configured such that the intrinsic brain potentials includes local field potentials.

In Example B22, the apparatus of one or any combination of Examples B19-B21 can optionally be configured such that the intrinsic brain potentials include intrinsic neuronal action potentials.

In Example B23, the apparatus of one or any combination of Examples B19-B22 can optionally be configured such that the brain potentials monitor circuit can comprise: separate electrodes, each electrode can include an integrated sensing circuit and an integrated digitizing circuit located at that electrode; and an ambulatory transmitter circuit located at the subject, the transmitter circuit can be communicatively coupled to the electrodes, the transmitter can be configured for wireless data transmission to a local or remote external receiver.

In Example B24, the apparatus of one or any combination of Examples B19-B23 can optionally be configured such that the brain potentials monitor circuit can comprise a multi-unit activity (MUA) monitor circuit that can be configured for monitoring neuronal activity of a set of nearby individual neurons.

In Example B25, the apparatus of one or any combination of Examples B19-B24 can optionally comprise a MUA monitor circuit that includes: a signal comparator, which can be configured for determining whether a neuronal signal energy indication exceeds a specified threshold value; and a counter, which can be coupled to the signal comparator, the counter can be configured to count a number of neuronal signal energy indications that exceed the specified threshold value.

In Example B26, the apparatus of one or any combination of Examples B19-B25 can optionally comprise an MUA monitor circuit that can comprise a signal integrator configured to integrate a neuronal signal over time.

In Example B27, the apparatus of one or any combination of Examples B19-B26 can optionally comprise at least one of the Normal template, the Non-Normal template, and monitoring circuit including a covariance determination circuit that can be configured to measure a covariance of a brain potential indication using at least two different locations of a brain of the subject.

In Example B28, the apparatus of one or any combination of Examples B19-B27 can optionally comprise an upcoming seizure prediction circuit that can include: a first comparator circuit, which can be coupled to the Normal template and the monitoring circuit, and which can be configured to compare an indication of correlation obtained during the sampling time period to an indication of correlation associated with the Normal template; a second comparator circuit, which can be coupled to the Non-Normal template and the monitoring correlation circuit, and which can be configured to compare an indication of correlation obtained during the sampling time period to an indication of correlation associated with the Non-Normal template; a seizure likelihood determination circuit, which can be coupled to the first and second comparator circuits, the seizure likelihood determination circuit can be configured to provide a greater likelihood of the upcoming seizure when the indication of correlation obtained during the seizure prediction becomes less closely matched to the indication of correlation of the Normal template and becomes more closely matched to the indication of correlation of the Non-Normal template; and an alert circuit, configured to provide an alert when the likelihood of the upcoming seizure exceeds a specified alert threshold value.

In Example B29, the apparatus of one or any combination of Examples B19-B28 can optionally comprise the Non-Normal template that is a Pre-Seizure template providing an indication of correlation of the brain potentials during at least one pre-seizure time period of the subject, wherein the pre-seizure time period is less or equal to a second specified time period before the seizure.

Example C1 can include subject matter that can include an apparatus comprising an electroencephalographic (EEG) monitoring kit comprising an EEG recording module, comprising a memory configured for recording a plurality of EEG signals from a patient. The EEG monitoring kit can further comprise a headpiece, configured such that the EEG recording module is capable of being mounted to the headpiece. The headpiece can comprise a head-receiving configuration of support members, the configuration of support members carrying a plurality of electrode assemblies that are electrically connected to the EEG recording module and that are capable of being individually relocated by a user from a first location on the patient's head to a different second location on the patient's head while the headpiece is in place on the patient's head.

In Example C2, the subject matter of Example C1 can optionally include at least one of the electrode assemblies comprising a plunger. The plunger can be configured to allow user-adjustment of an electrode toward a scalp of the patient.

In Example C3, the subject matter of any one or more of Examples C1-C2 can optionally include at least one of the electrode assemblies comprising a plunger. The plunger can be configured to allow user-actuated release of an at least somewhat flowable conductive substance toward a skin-electrode interface such as to assist in obtaining good electrical conduction at the skin-electrode interface.

In Example C4, the subject matter of any one or more of Examples C1-C3 can optionally include at least one of the electrode assemblies comprising an accelerometer.

In Example C5, the subject matter of any one or more of Examples C1-C4 can optionally comprise a signal processing circuit, which can be coupled to the accelerometer. The signal processing circuit can be configured to detect relative motion of that electrode assembly beyond motion of the patient's head or body.

In Example C6, the subject matter of any one or more of Examples C1-C5 can optionally comprise the EEG recording module comprising an impedance test circuit. The impedance test circuit can be configured to measure a skin-electrode impedance of an individual electrode configured to provide an EEG signal.

In Example C7, the subject matter of any one or more of Examples C1-C6 can optionally comprise the impedance test circuit being configured to measure the skin-electrode impedance of the individual electrode. The measurement of skin-electrode impedance of the individual electrode can be independent of a skin-electrode impedance of a reference electrode, and independent of an skin-electrode impedance of a ground electrode.

In Example C8, the subject matter of any one or more of Examples C1-C7 can optionally comprise a user interface capable of being communicatively coupled to the memory of the EEG recording module and configured to receive information from the recorded plurality EEG signals. The user interface can include or can be configured to be coupled to a camera to obtain images of the patient to be stored in concordance with the plurality of EEG signals.

In Example C9, the subject matter of any one or more of Examples C1-C8 can optionally include the EEG recording module including a non-EEG physiological sensor interface configured to receive at least one non-EEG physiological signal. The EEG recording module can be configured to record the non-EEG physiological signal in concordance with the plurality of EEG signals.

In Example C10, the subject matter of any one or more of Examples C1-C9 can optionally include at least one of the electrode assemblies including a threaded receptacle and a flange. The flange can be configured to slide with respect to one of the support members (e.g., such as along a slot or rail or the like), such as to permit that electrode assembly to be individually relocated by the user from the first location on the patient's head to the different second location on the patient's head while the headpiece is in place on the patient's head.

In Example C11, the subject matter of any one or more of Examples C1-C10 can optionally include at least one of the electrode assemblies including a liquid-absorbing electrode to receive a flowable conductive substance to enhance skin-electrode conductivity.

In Example C12, the subject matter of any one or more of Examples C1-C11 can optionally include the EEG recording module that is capable of being mounted to the headpiece comprising: an automatic gain control (AGC) circuit configured to automatically adjust the gain of each of the plurality of EEG signals being recorded from the patient; an analog-to-digital converter (ADC) circuit, configured to digitize the plurality of automatic-gain-controlled EEG signals before recording; and a memory circuit, configured to record the plurality of EEG signals.

In Example C13, the subject matter of any one or more of Examples C1-C12 can optionally include the headpiece including a local position monitor configured to monitor the user-adjustable position of one of the electrode assemblies and to provide an indication of the position of the electrode assembly to the memory of the EEG recording module for recording.

In Example C14, the subject matter of any one or more of Examples C1-C13 can optionally include an adjunct computing device, capable of being communicatively coupled to the memory of the EEG recording module and configured to receive information from the recorded plurality of EEG signals. The adjunct computing device can include or can be configured to be coupled to processor configured to perform seizure detection using information from the recorded plurality of EEG signals.

In Example C15, the subject matter of any one or more of Examples C1-C14 can optionally include the adjunct computing device being configured to be communicatively coupled to a plurality of EEG recording modules.

In Example C16, the subject matter of any one or more of Examples C1-C15 can optionally include an adjunct computing device that can include or can be coupled to a memory circuit that can include instructions that, when performed by a processor circuit of the adjunct computing device, analyzes EEG signals from the plurality of EEG recording modules associated with different patients such as to prioritize patients for further attention.

In Example C17, the subject matter of any one of Examples C1-C16 can optionally include an adjunct computing device that can include or can be coupled to a memory circuit including instructions that, when performed by a processor circuit of the adjunct computing device, records a measure of performance of a plurality of human reviewers.

These non-limiting examples can be combined in any permutation or combination. This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

System Overview

Figure 1:
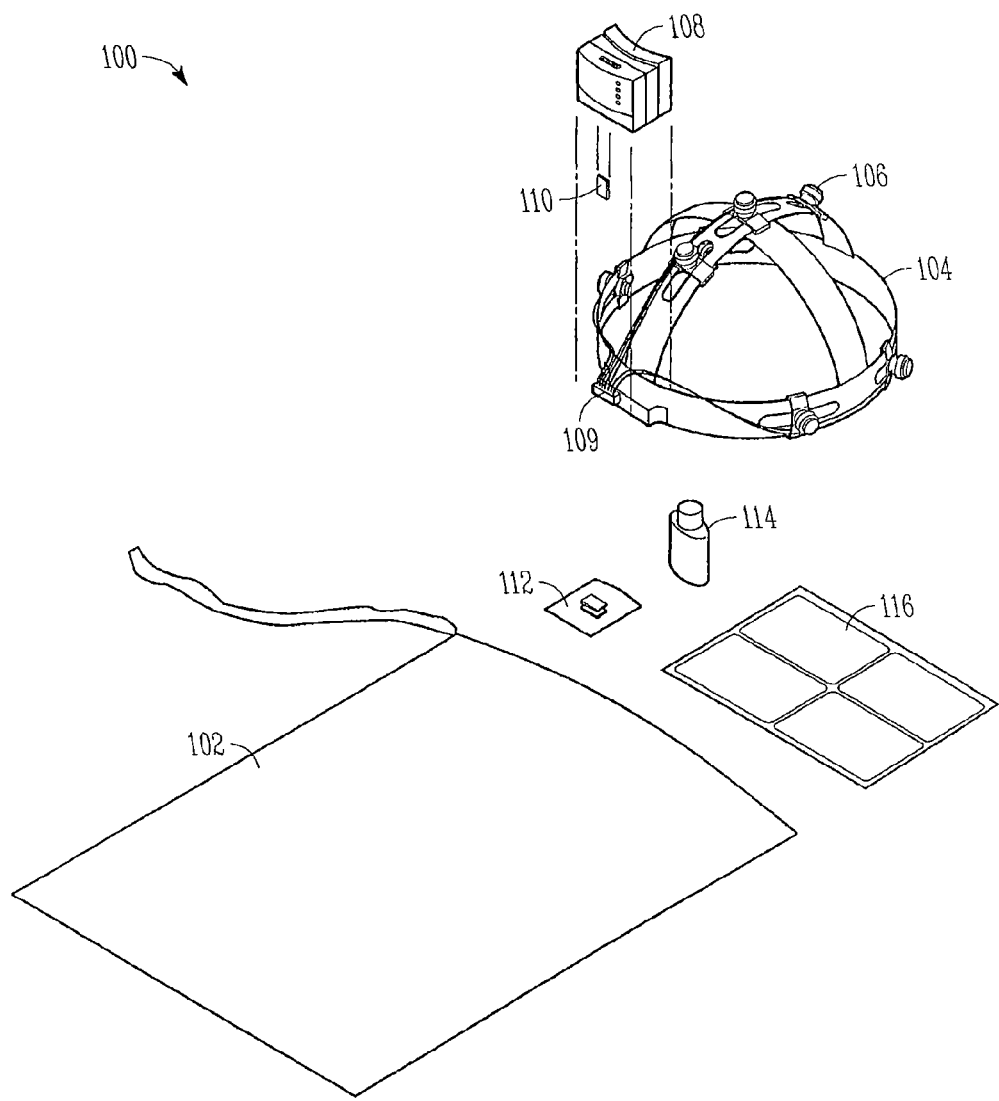
FIG. 1 shows an example of portions of the present system, including an EEG kit that can include sterilized components that can be packaged together in a kit, which can include a sterilized package such as a plastic bag.

FIG. 1 shows an example of portions of the present system, including an EEG kit 100 that can include sterilized components that can be packaged together in a kit package, which can provide or carry or include an internally sterilized package such as a plastic bag 102. In an example, such components in the EEG kit bag 102 can include a headpiece 104, which can include multiple electrodes 106. In an example, the multiple electrodes 106 can be fixedly or adjustably pre-mounted onto the headpiece 104. An EEG recorder 109 assembly can be included in the kit bag 102 and can be pre-mounted onto the headpiece 104 or easily user-connectable thereto, such as via an electrical and mechanical dock connector 109 that can be located on the headpiece 104. The EEG recorder 108 can be configured to do one or more of acquiring individual EEG signals from respective electrodes 106, storing information about one or more such EEG signals in an onboard memory circuit that can be included in the EEG recorder 108, signal-processing one or more such EEG signals, or wirelessly communicating information about one or more such EEG signals from the EEG recorder 108 to an auxiliary device. A memory card 110 can be included in the kit bag 102 and can be pre-inserted into the EEG recorder 108, or easily user-insertable therein. Spare memory cards can also optionally be provided in the kit bag 102, such as in a separate sealed bag. A bottle of saline solution 114 can be provided in the kit bag 102, such as to help make good conductive contact between one or more of the EEG electrodes 106 and the patient's scalp. An instruction card 116 can be provided in the kit bag 102, such as to provide instructions for use in the emergency department or another setting.

Even though the components provided in the EEG kit bag 102 can be considered disposable, the EEG recorder assembly 108, which can include a processor circuit, memory circuit, other electronics, and a battery, can optionally be salvaged such as for refurbishment, such as by a third party service provider, who can refurbish the EEG recorder 108 and place it back into the supply stream for the present system. An example of electronics, telemetry, signal processing and the like that can be included in the EEG recorder 108, in an example, is described in James G. Donnett et al. U.S. patent application Ser. No. 11/694,816, entitled BRAIN SIGNAL TELEMETRY AND SEIZURE PREDICTION, filed on Mar. 30, 2007, which is hereby incorporated herein by reference in its entirety. Briefly, U.S. patent application Ser. No. 11/694,816 describes an ambulatory intrinsic brain signal processor circuit is coupled to a plurality of electrodes. The signal processor circuit can include a digital multiplexer circuit coupled to the electrodes to multiplex brain signal data from different electrodes together into a multiplexed data stream. An ambulatory transceiver circuit wirelessly communicates information to and from a remote transceiver. A controller circuit permits a user to control which of the electrodes contribute data, a data resolution, and whether the data includes one or both of neural action or local field potential data. Seizure prediction components and methods are also described. While U.S. patent application Ser. No. 11/694,816 emphasizes seizure prediction, its systems and methods can also be used to diagnose a seizure that is already present.

Figure 2:
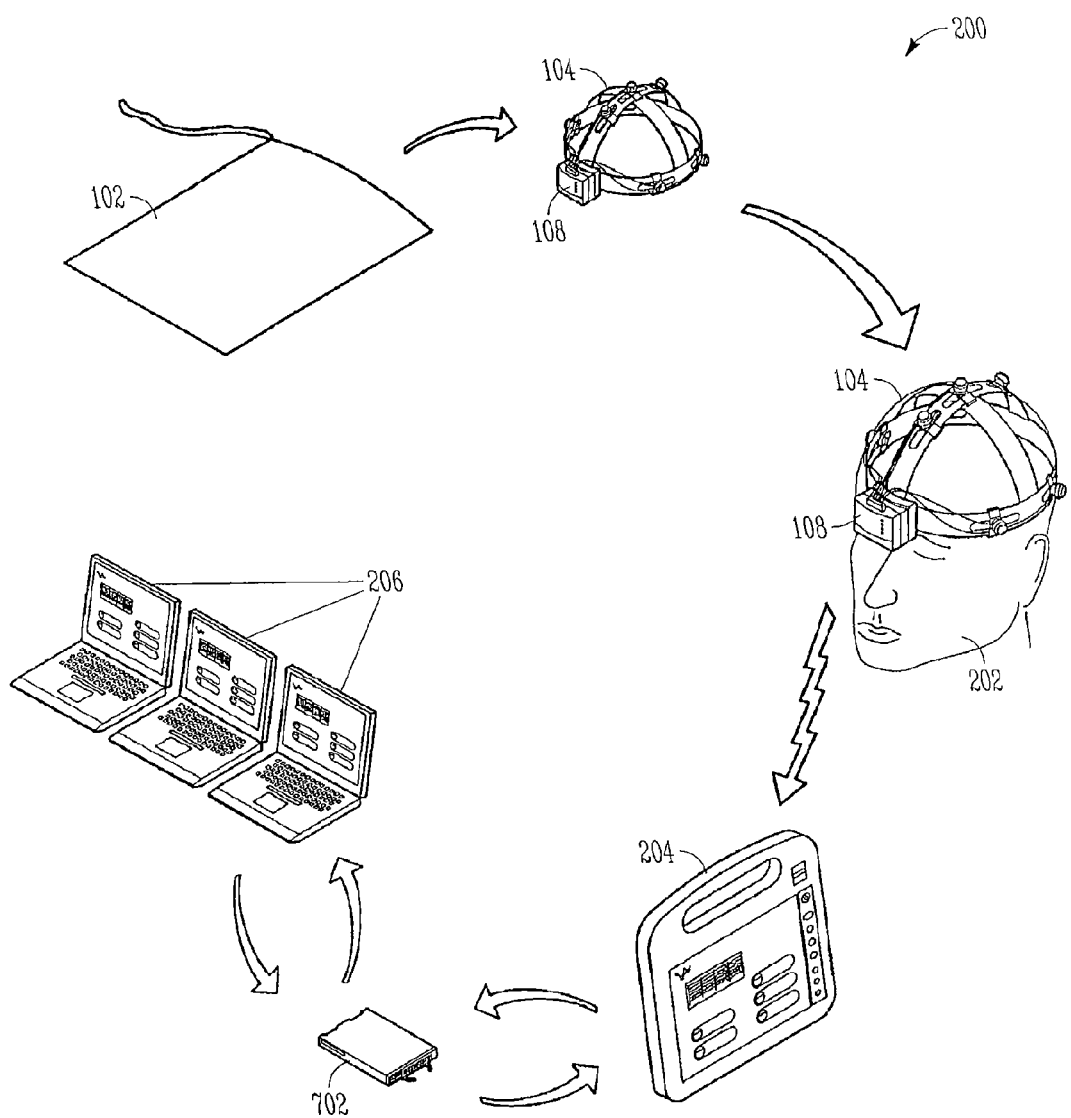
FIG. 2 shows an example of portions of the present system, in which the EEG kit bag has been opened to remove the headpiece and the EEG recorder that can be mounted thereto, such as to allow data acquisition and communication with a local or remote adjunct device.

FIG. 2 shows an example of portions of the present system 200, in which the EEG kit bag 102 has been opened to remove the headpiece 104 and the EEG recorder 108 that can be mounted thereto. The headpiece 104 can be mounted to a head of a patient 202, such as in the hospital emergency department. The EEG recorder 108 can wirelessly transfer recorded EEG information to a local user interface 204, such as by using a Bluetooth or other wireless modality. The local user interface 204 can include a display that can be configured to be capable of graphically displaying EEG information or information derived at least in part therefrom. In an example, the local user interface 204 can also include a memory circuit and a processor circuit or other signal processing circuitry configured to process the EEG information such as to automatically determine whether a seizure or other neurological condition is present, and to display or otherwise present such resulting diagnostic information. An example of electronics, signal processing, and other circuits and techniques for determining whether a seizure condition is present or impending is described in James G. Donnett et al. U.S. patent application Ser. No. 11/694,855, entitled SEIZURE PREDICTION USING BRAIN SIGNAL TELEMETRY, filed on Mar. 30, 2007, which is hereby incorporated herein by reference in its entirety.

The local user interface 204 can also be coupled to a wired or wireless computer or communications network, such as the internet, such as to transfer the EEG information to one or more remote user interfaces 206. In an example, the remote user interface 206 can also include a memory circuit, a processor circuit, or other signal processing circuitry such as can be configured to process the EEG information such as to automatically determine whether a seizure or other neurological condition is present, and to display or otherwise present such resulting diagnostic information. An example of electronics, signal processing, and other circuits and techniques for determining whether a seizure condition is present or impending is described in James G. Donnett et al. U.S. patent application Ser. No. 11/694,855, entitled SEIZURE PREDICTION USING BRAIN SIGNAL TELEMETRY, filed on Mar. 30, 2007, which is hereby incorporated herein by reference in its entirety.

In an example, the remote user interface can be used by a neurologist capable of diagnosing the EEG information, such as to determine whether a seizure condition or other functional brain abnormality is present. The neurologist can be located within the same hospital, within the local community (e.g., at home, at a practice location, etc.) or anywhere else in the world to where such information can be communicated by the communications or computer network. The neurologist's diagnosis can, in return, be communicated back to the emergency department, where it can be used to appropriately initiate or adjust treatment of the patient.

Although FIG. 2 shows the local user interface 204 as not being included in the EEG kit bag 102, in another example, the local user interface 204 can also be included in the EEG kit bag 102. In either case, the local user interface 204 can optionally also include signal processing software such as for automatically diagnosing whether a seizure condition is present in the patient 202, such that remote diagnosis using the remote user interface 206 is not required, but can still optionally be used such as for remote verification by a neurologist of the automatic local diagnosis, if desired. The signal processing and automatic diagnosis can also be performed at a remote processor, such as the remote user interface 206, or a remote computer server, if desired.

In an example, the local user interface 204 can include an integrated or attached video camera, such as to capture video of the patient in conjunction with the recording of the EEG. The video information can also be communicated with the EEG information to the remote user interface 206, where it can be displayed, such as to help the neurologist in diagnosing whether a seizure condition is present.

In an example, either the local EEG recorder assembly 108 or the local user interface 204 can also include an interface such as to receive information from a different physiological sensor such as a finger cuff or other pulse oximeter, such as to acquire different physiological information such as blood oxygen level information. The blood oxygen level or other different physiological information can also be communicated, such as with the EEG information, to the remote user interface 206, where it can be displayed, such as to help the neurologist, such as in diagnosing whether a seizure condition is present.

In an example, either the local EEG recorder assembly 108 or the local user interface 204 can also include an interface such as to receive information from chest electrode leads or other implantable, wearable, or other ambulatory electrocardiogram (EKG) monitor, such as to acquire heart signal information. The heart signal information can also be communicated, such as with the EEG information, to the remote user interface 206, where it can be displayed, such as to help the neurologist in diagnosing whether a seizure condition is present.

Headpiece, EEG Recorder, and Electrode Assemblies

Figure 3:
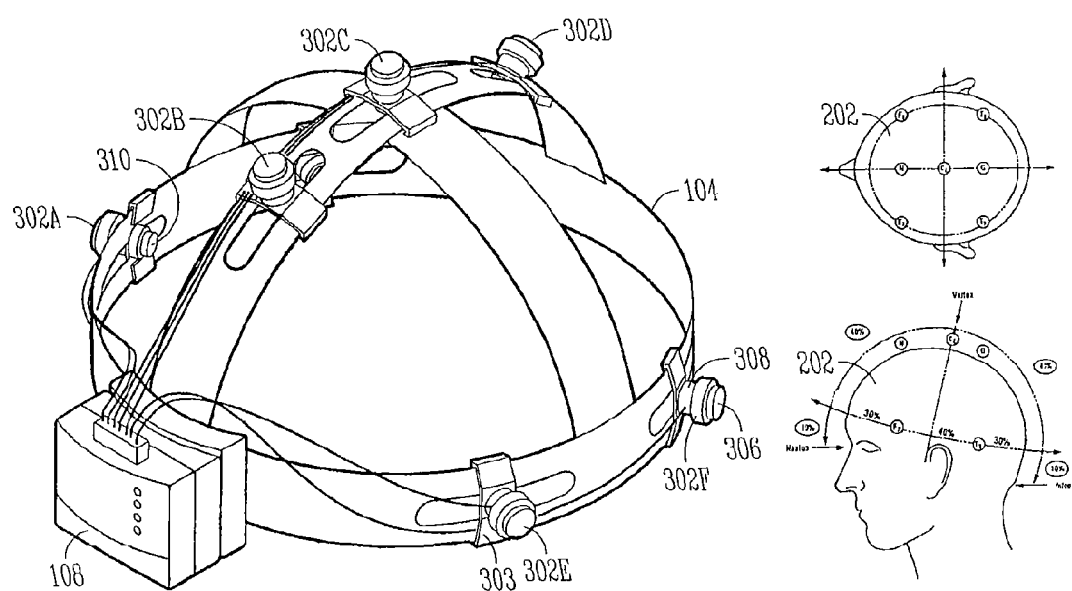
FIG. 3 shows an example of the headpiece and its mounted EEG recorder, and potential electrode locations when viewed from the side of the patient and when viewed from the top of the patient.

FIG. 3 shows an example of the headpiece 104 and its mounted EEG recorder 108, and potential electrode locations when viewed from the side of the patient 202 and when viewed from the top of the patient 202. In the example of FIG. 3, the EEG recorder 108 can be locally mounted to the head piece 104 placed on a patient's head, and can use a "minimal" or other subset of scalp contact electrodes, as compared to a conventional 10-20 EEG electrode montage. The sparse electronics and small capacity battery of the EEG recorder 108 can be carried within and fully covered or housed by an enclosure. The electrodes on the head piece 104 can be individually electrically connected by respective conductive wires 303 to the nearby-mounted EEG recorder 108, with the relatively short lengths of the conductive wires 303 allowing recording in an electromagnetically "noisy" emergency room environment without coupling in too much noise. The EEG recorder 108 can include an onboard recording device, such as can include a flash memory or other memory circuit, or information can be transferred wirelessly from the EEG recorder assembly 108 to the local user interface 204. By minimizing the length of the analog-signal path, this digital, compact, and wireless approach can reduce electrical interference or "noise" associated with currently used equipment, which employs a tethered bundle of wiring leading from a cap to a non-ambulatory or ambulatory recording device that is not locally mounted to a headpiece on the patient's head.

The headpiece 104 can include fixed or adjustably positionable electrode assemblies 302, for example, that ride along a track such as a position adjustment slot 304 or rail or the like. The electrode assemblies 302 can include single-use or other similar electrodes that can be configured for short-term (e.g., 10 to 20 minutes) recording associated with the emergency department application, as compared to a long term clinical application. An electrode assembly 302 can include a built-in plunger, such as to move the electrode inward toward the scalp, such as to help make contact with the scalp after the headpiece 104 has been placed on the patient's head. In an example, this can be accomplished by the plunger having ¼ turn or other locking threads that engage threads in a plunger receptacle. The plunger can be pushed, such as to make contact with the scalp, then turned, such as ¼ rotation, thereby locking into segmented threads. Continuous threading would require continuous turning and could "screw" the patient's hair into a knot. In an example, depressing a plunge cap 306 or other portion of the plunger can actuate puncture or other opening of a sterile plastic sleeve or other reservoir 308 that can release a sterile electrically conductive substance (e.g., saline solution, colloidal paste, or the like) such as to quickly and conveniently help provide good conductive contact between the electrode and the patient's scalp.

In an example, the electrode contacting the scalp can include a quick and convenient single-use foam or sponge plug electrode 310, which can be actuated by the plunger, such as described above. In an example, the foam or sponge plug electrode 310 can include a phenolic or other water absorbent foam that can receive saline solution from the reservoir 308 such as to help provide good electrical conduction through the foam or sponge plug electrode 310 and with the scalp. The foam or sponge can be used as alternatives or in combination with each other or in combination with another material.

In an example, one, several, or each individual electrode assembly 302 can be multiplexed or otherwise coupled to an impedance sensing circuit so as to be configured to provide, e.g., during setup or ongoing, impedance monitoring (e.g., continuous, periodic, recurrent, etc.) of the impedance provided by the electrode of that electrode assembly. This can include such impedance monitoring of the ground or reference electrodes. In an example, each electrode's impedance can be measured independently of the impedance of the electrode assemblies 302 that are respectively designated as "ground" and "reference." Such impedance measuring can be carried out by the impedance sensing circuit in the EEG recorder assembly, such as by initially, occasionally, or continuously injecting a test current via a particular pair of electrodes, and measuring a response voltage, from which an impedance can be calculated using Ohm's Law, such as by a processor circuit onboard the EEG recorder assembly 108 that can be coupled to the impedance sensing circuit by an analog-to-digital converter to digitize the sensed impedance signal. The processor circuit can also cycle between carrying out the impedance measurements from various different electrode pairs, such as for better determining the impedance at a particular electrode-skin interface. This can be accomplished by multiplexing the various different electrode pairs to the impedance sensing circuit, such as under control by the processor circuit.

Impedance measurements can help inform the user whether a good electrically conductive contact to the scalp is present for EEG monitoring, or whether poor electrode-skin contact impedance exists, indicating a need for additional conductive substance, such as the spare saline solution 114, moving of the electrode assembly 302, or other corrective measure. When the impedance is inappropriate, an alarm can be provided to the user, and the impedance state can be stored in the data record so that this impedance-related information can be used by software or the user reading the EEG to help correctly interpret the signals from such an electrode. In an example, a user-discernable indication of the electrode impedance can be presented to the user such as visually, such as via a light emitting diode (LED) or other visual display indicator located on the electrode assembly or located on the housing of the EEG recorder 108 or user interface (UI). Such automatic sensing of electrode placement quality can allow subject-specific placement of the montage of electrode assemblies 302 for quickly and easily obtaining good EEG signal information. In an example, the EEG recorder 108 electronics can include an automatic gain control (AGC) circuit that can modulate the amplitude of the acquired EEG signals, such as to help ensure adequate or optimal dynamic range of the acquired EEG signals. The EEG recorder 108 can represent the EEG data in a data format that can represent the variable gain data (such as together with information about the gain setting being used for acquisition of such data) such as can be provided by the AGC circuit.

Figure 4A:
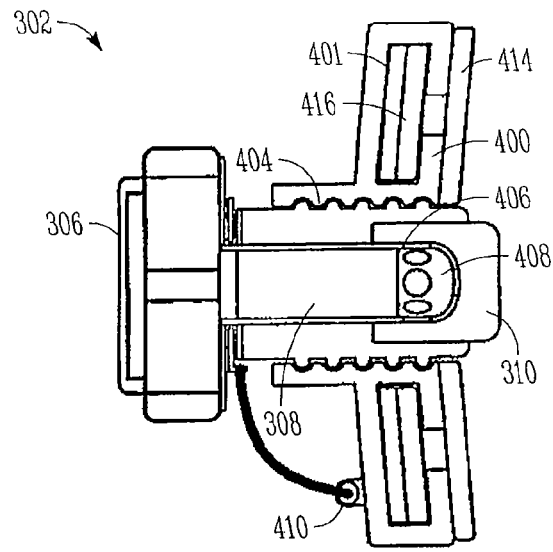
FIG. 4A is an example of a cross-sectional view of an example of an electrode assembly.

FIG. 4A is an example of a cross-sectional view of an example of an electrode assembly 302, an internally-threaded receptacle 400 of which can include a flange 430 portion extending therefrom that can ride on a track such as on a headband 401 or other member of the headpiece 104. In an example, turning the plunger handle 402 can depress the threaded plunge/plunger 404, such as via the threaded engagement with the receptacle 400. This can move the foam plug 310 toward and into physical contact with the scalp. Depressing the plunge/plunger cap 306 can rupture a seal such as an internal frangible seal 406. This can release the sterile saline or other conductive substance from the reservoir 308, such as via an electrically conductive delivery channel 408 within the receptacle 400. The electrically conductive substance can soak into the foam plug 310 that can serve as the portion of the electrode contacting the scalp, such as to help provide good electrical conduction through the foam plug 310. A proximal portion of the conductive delivery channel can be electrically coupled to one or more wires 410, such as can lead to the EEG recorder 108 or to an impedance-indicating LED 412. An absorbent O-ring 414 can be located under a flange 430 portion of the receptacle 400, and an absorbent band 416 can be provided within the flange 430 portion of the receptacle 400, such as under the headband 401. This can help inhibit or prevent leakage of a liquid conductive substance such as the saline in the reservoir 308 from the electrode site on the scalp. This, in turn, can help inhibit or prevent electrical communication between the different electrode assemblies 302 via blood or sweat or via conductive fluid that has leaked out onto the scalp beyond the electrode site at which the particular electrode assembly 302 is located.

Figure 4B:
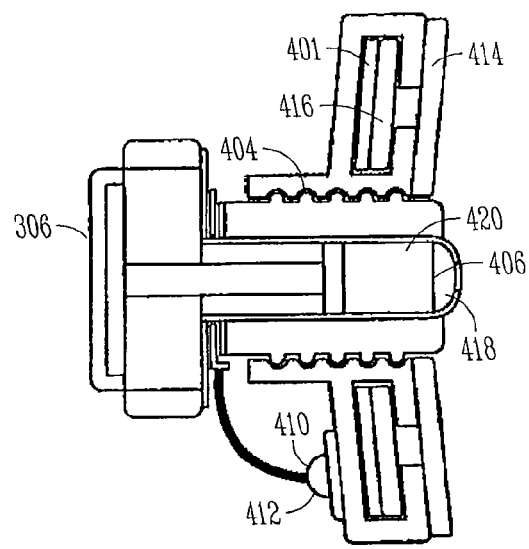
FIG. 4B is another example of a cross-sectional view of another example of an electrode assembly.

FIG. 4B is an example of a cross-sectional view of an example of an electrode assembly 302, similar to that shown in FIG. 4A. However, in this example, the foam plug 310 and the liquid reservoir 308 can be omitted. Instead, the electrode-skin contact can be made by an electrically conductive delivery channel 418 that can carry a less flowable electrically conductive substance than the saline in the reservoir 308, such as a conductive colloidal paste 420 or electrode gel, which can be formed into a plug that can be located behind the internal frangible seal 406. The plunge/plunger cap 306 can be depressed, such as to rupture the seal such as the internal frangible seal 406. This can release the paste 420 toward the scalp to promote a good electrically conductive skin-electrode contact between the scalp and the electrically conductive delivery channel 418, which can, in turn, be wired to the EEG recorder 108 or to an impedance sensing circuit that can output impedance information such as to drive the impedance monitoring LED 412.

Figure 4C:
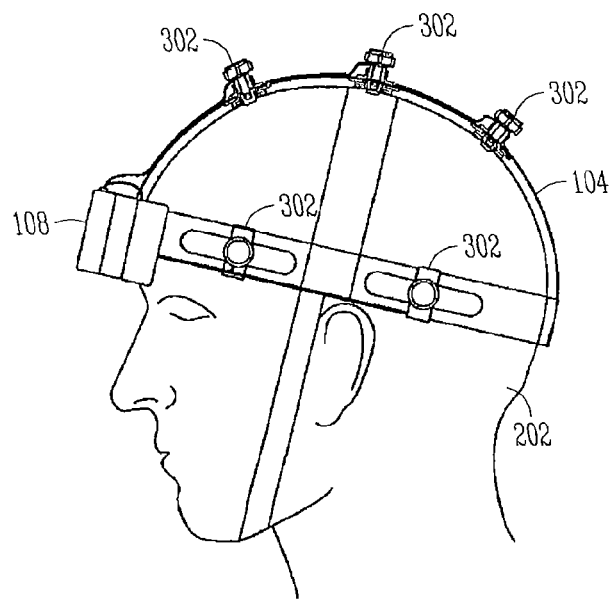
FIG. 4C shows an example of the headpiece that has been quickly and conveniently mounted on the head of a patient, showing an example of possible locations of the electrode assemblies.

FIG. 4C shows an example of the headpiece 104 that has been quickly and conveniently mounted on the head of a patient 202, showing one example of possible locations of the electrode assemblies 302 on the patient's scalp.

Figure 4D:
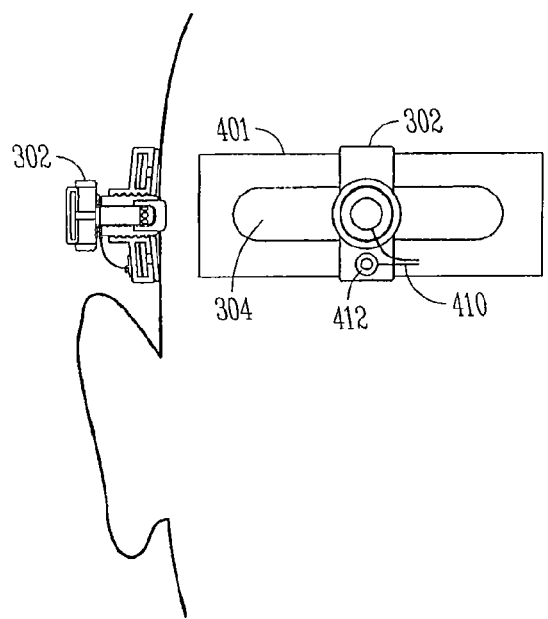
FIG. 4D shows an example of a cross section of an electrode assembly, located against the side of a patient's head, in this example, along with an illustrative portion of a headband of the headpiece.

FIG. 4D shows an example of a cross section of an electrode assembly 302, located against the side of a patient's head, in this example, along with an illustrative portion of a headband 401 of the headpiece 104. In this illustrative example, the electrode assembly 302 can travel on a track, such as about 25 millimeters in either direction from a centered location within the position adjustment slot 304. This can help the user obtain a location of good skin-electrode contact or to avoid an injured portion of the head of the patient 202. In an example, the actual position of the electrode assembly 302 can be automatically sensed, such as via a potentiometer or other electronics that can be located in the position adjustment slot 304. This can permit the electrode position relative to one or more physical landmarks on the patient's head (such as nasion and inion) to be automatically determined and optionally stored with the EEG data. Knowledge of the precise electrode position can help to correctly interpret the clinical significance of EEG events. This feature of automatic sensing of electrode position can also be used in conjunction with the UI device 204, such as to permit the UI device 204 to interactively guide the user to correctly place the electrode at a predetermined or desired site, for example, corresponding to one of the 10-20 scalp electrode placements discussed above, or at one or more other desired sites on the patient's scalp.

User Interface Device

The local user interface device 204 can be configured with stored instructions such that it can be used to do one or more of: procedure setup, input patient data, review the EEG recording, and forward EEG recording information to the remote user interface 206 or the remote server. In an example, a third party laptop computer, smart phone or personal digital assistant (PDA) device, net book, (e.g., the Lenova S-series IdeaPad), or medical grade tablet PC (e.g., the Motion C5) can be used. An integrated or attachable web camera can be provided with the local user interface device 204, such as to allow the local user to create a video record of the patient, which can be stored as synchronized to or in correspondence with the recorded EEG or different other physiological data, such as for assisting in diagnosis or documentation. In an example, the user interface device can include a video or other data compression circuit such as to perform data compression of the full-body video, which, in an example, can be reduced to 3-5 frames per second (FPS), such as from a recording at 30 FPS, such as to reduce the video file size.

In an example, the local user interface device 204 can be configured with stored instructions such that a caregiver or other local user can also create text, voice, graphical or other notes or annotations, which can also be stored in correspondence with the recorded EEG data, such as to further diagnose or document the physical state of the patient as the EEG data is acquired or reviewed. Also, as described above, other physiological sensor data (e.g., oxygen saturation, heart rate, heart signal, etc.) can be acquired and stored in correspondence with the EEG data, such as to further assist diagnosis or documentation.

In an example, the local user interface device 204 can be configured to include an easy to use and interactive program to instruct or assist the local user in using the EEG kit 102 or system 200. For example, using video, animation, graphics, or voice-over, a multi-layered interactive tool can be provided. This can help the local end-user navigate one or more of the following:

A. Selecting the correct size EEG Kit bag 102 (e.g., infant/child/adult)—in an example, within each such designated size, the headpiece 104 can be elastic enough to expand to fit a range of head sizes or shapes;

B. Placing or fitting the headpiece 104 onto the patient 202;

C. Adjusting the position of one or more electrode assemblies 302, if desired, or as required;

D. Pressing the plunge cap 306 on each electrode assembly 302, such as to introduce the on-board conductive saline solution or conductive paste into or about the scalp contact at each location of electrode assembly 302;

E. Attaching the EEG recorder 108 to the head piece 104, such as if not pre-attached thereto;

F. Performing an initial impedance check on the electrodes of the electrode assemblies 302, such as by running an impedance check script that can be actuated by the end user, such as by a user control that can be provided at the EEG recorder 108 or at the local user interface device 204;

G. Recording EEG information from the patient 202;

H. Transferring EEG information from the EEG recorder 108 to the local user interface device 204, such as for review, automatic or manual diagnosis, or EMR documentation using the local user interface device 204, or after transfer over a wireless or wired computer or communications network to the remote user interface device 206 or a remote computer server, or transferring data to on-board data storage, such as a removable memory card 110 that can be provided at the EEG recorder 108 or at the local user interface device 204;

I. Uploading EEG recording or other physiological data or patient information to the remote user interface device 206 or a remote computer server, such as over a wireless or wired computer or communications network or using the removable memory card 110;

J. Retrieving a diagnosis, which can be based at least in part on the recorded EEG data, for example, provided by a remote diagnosing neurologist using the remote user interface device 206, or provided by automatic processing of the recorded EEG data or other data at the local user interface device 204 or the remote user interface device 206; or K. Repacking some or all of the used components back into the EEG kit bag 102, which can be re-sealable, such as for disposal or reclamation.

Example of Method of Use

Figure 5:
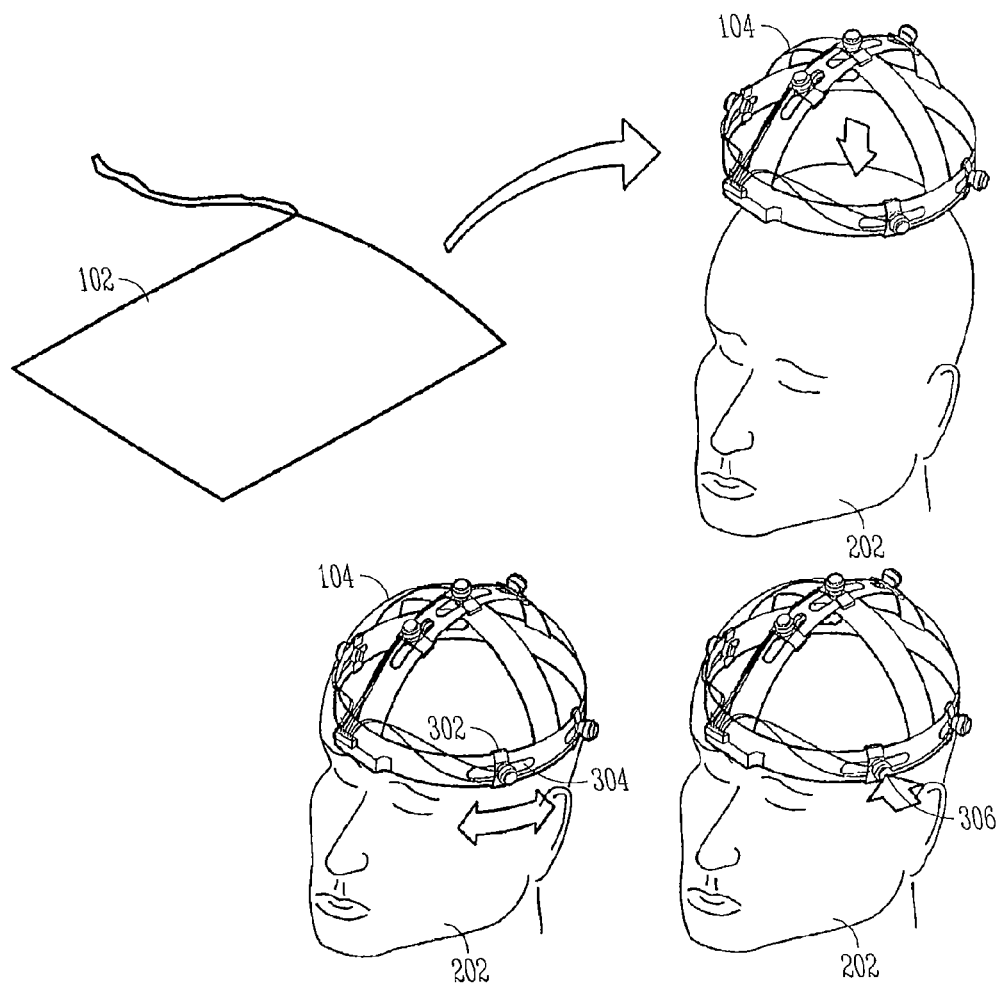
FIG. 5, FIG. 6, FIG. 7, and FIG. 8 illustrate an example of a method of using all or portions of the system, such as in a hospital emergency department setting.

FIGS. 5-8 illustrate an example of a method of using all or portions of the system 200, such as in a hospital emergency department setting. In FIG. 5, at step 1, an EEG kit bag 102 can be ordered or retrieved in the emergency department. This can involve selecting from differently sized EEG kit bags 102, such as infant, child, and adult sizes, or sized for a specific head diameter or a specific range of head diameters or the like.

At step 2, the selected EEG kit bag 102 can be opened, the headpiece 104 can be removed from the selected EEG kit bag 102, and the headpiece 104 can be fitted onto the head of the patient 202.

At step 3, in an example, the positions of one or more of the electrode assemblies 302 can be adjusted, if desired, such as by moving the electrode assembly along one of the positioning slots 304. In an example, seven electrodes can be used, for example, five signal electrodes and a reference and a ground electrode. Position adjustment of an electrode assembly 302 can be desired, such as to conform to sites in the 10-20 standard for electrode placement, or to establish a position where a good electrical electrode-scalp contact can be made, or to target or avoid an injury site, or for any other desired reason.

At step 4, the plunge cap 306 on each of the (e.g., seven) electrode assemblies 302 can be pressed, such as to introduce the on-board saline solution, electrode gel, or colloidal paste into the electrode-scalp interface at each electrode position of the electrode assemblies 302. The plunger 304 can be pushed inward for scalp contact, then turned, such as by ¼ rotation, thereby locking into segmented threads of the threaded receptacle 400 at either of steps 3 or 4 to move the electrode toward the head, if needed. This combination of plunging and turning can help avoid screwing the patient's hair into a knot, such as if a continuous threading involving extensive rotation were used to move the electrode toward the head.

Figure 6:
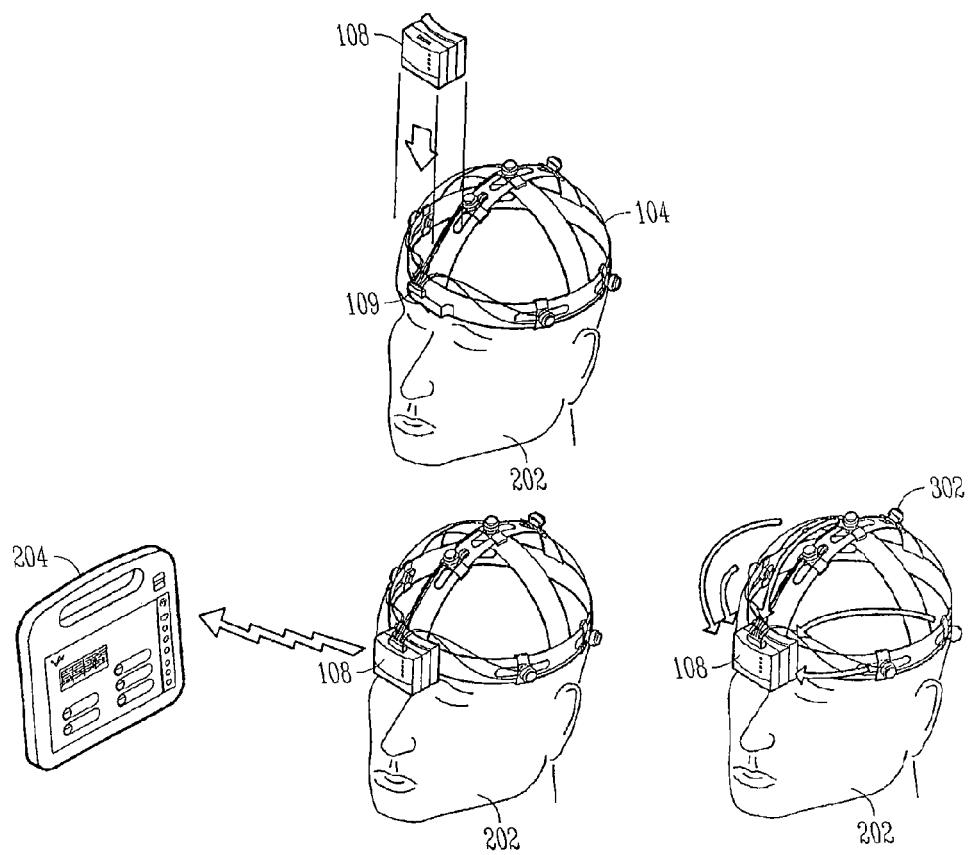

At step 5, shown in FIG. 6, the EEG recorder 108 can be quickly and easily attached to the headpiece 104, if not already pre-attached, such as at the recorder/electrode electrical and mechanical dock connector 109 that can be located on the headpiece 104 and individually pre-wired to the various electrode assemblies 302.

At step 6 of FIG. 6, the impedance of each electrode-scalp connection (including the ground and reference electrodes) can be checked, such as by manually (e.g., by the user) or automatically (e.g., by the local user interface 204 or the recorder assembly 108) initiating execution of an impedance checking script, for example, on a processor circuit of the local user interface device 204 (or by a circuit in the recorder assembly 108), which can wirelessly communicate with the EEG recorder 108, such as via a Bluetooth or other wireless communication link. The electrode assemblies 302 can be adjusted, if needed, such as by repositioning along the positioning slot 304, by pressing the plunger 304 toward the head, by depressing the plunge cap 306 to release a conductive substance, or by introducing a conductive substance, such as by using the extra saline or gel solution 114.

A calibration check can be performed, such as by acquiring EEG signals and determining the appropriate gain or filtering to be applied to obtain good quality or good resolution EEG signals for recording for performing the diagnosis.

At step 7 of FIG. 6, EEG signal recording can be user-initiated or automatically initiated. EEG signals can then be acquired at the electrode assemblies 302 and communicated via respective electrical wires to the EEG recorder 108, where such signals can be recorded, and then EEG signal recording can be terminated automatically (e.g., after a specified period of time, or after enough diagnostic data has been acquired) or by the user.

Figure 7:
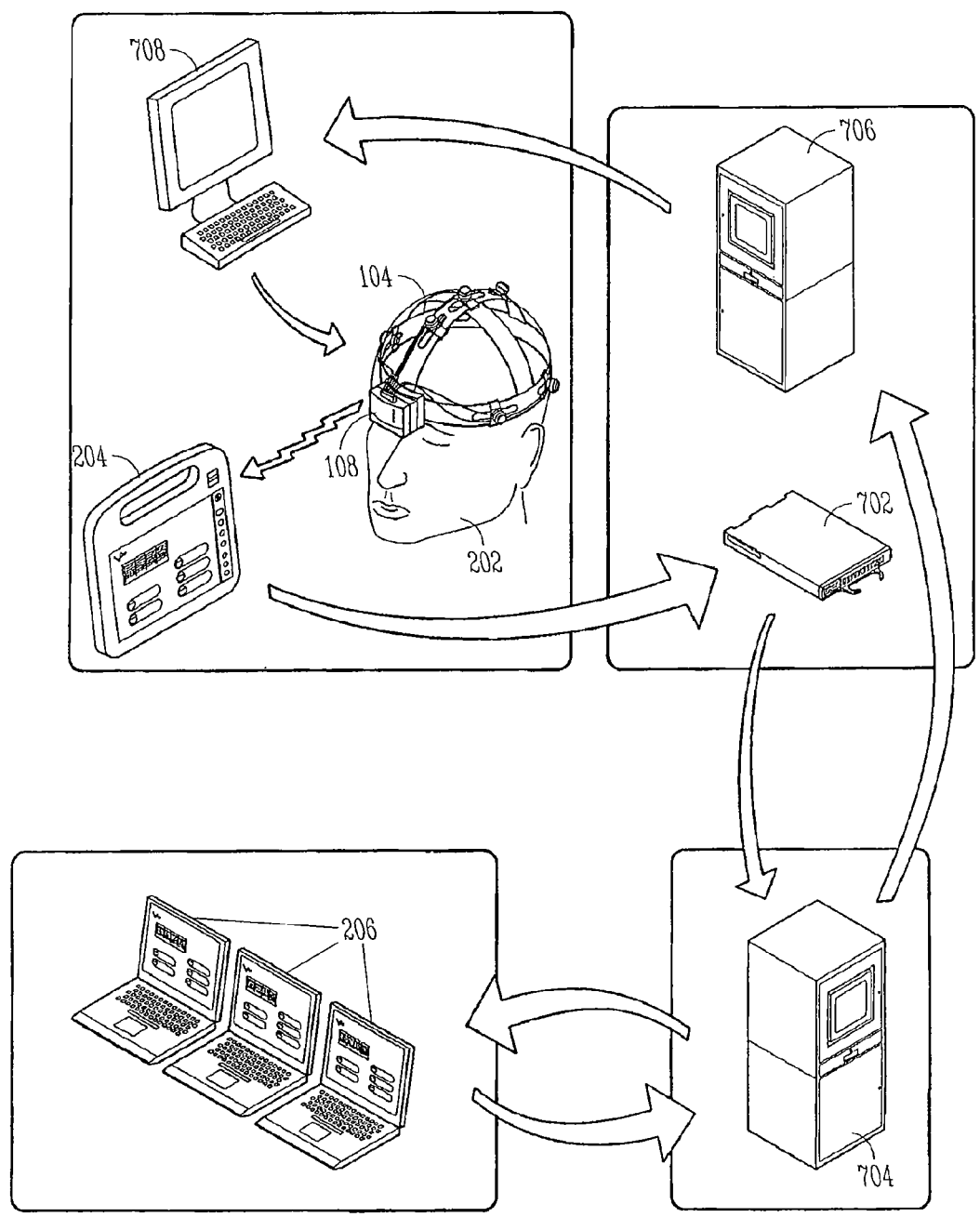

At step 8, shown in FIG. 7, the recorded EEG information can be transferred from the EEG recorder 108 to the local user interface device 204. This can be accomplished wirelessly, using a removable memory card, by using a wired galvanic or optical connection, or by any other suitable transfer technique. The emergency department physician can review the EEG signal information, or information or a diagnosis derived using the EEG signal information, which can be displayed on a display of the local user interface device 204.

At step 9A, of FIG. 7, the recorded EEG information or other patient information can be uploaded via a wired or wireless communication or computer network, such as a local area network (LAN), to a remote data collection device 702, such as a computer or server or the like that can be located elsewhere within the hospital. In an example, the remote data collection device 702 can include a processor circuit, a memory circuit, and other electronics, such as for implementing an electronic neurologist network (e-NN) management system, such as described further below.

At step 9B of FIG. 7, such recorded EEG information or other patient information can be encrypted and transferred over a wireless or wired computer or communications network, such as via a wide area network (WAN) such as the internet, to a third party remote server 704.

At step 9C of FIG. 7, the recorded EEG and optionally other patient physiological or other information can be used by an automatic process at the remote server 704 to diagnose whether a seizure is present. Note that this automatic diagnosis can also be made at the EEG recorder assembly 108 such as by implementing therein the appropriate digital signal processing computations. The automatic diagnostic process when implemented at the remote server 704, can involve comparing and resolving redundant diagnoses, checking the diagnosis against known examples, or other verification procedures. The resulting automated diagnosis can be encrypted and transferred, at step 9H, over a wireless or wired computer or communications network, such as via a wide area network (WAN) such as the internet, to a hospital server 706. At step 9I, the diagnosis can be relayed over the hospital LAN to a computer terminal 708 located in the emergency department of the hospital. At step 10, in accordance with the diagnosis, the emergency department physician can request or provide appropriate treatment to the patient 202.

At step 9D of FIG. 7, the recorded EEG and optionally other patient information can be encrypted and transferred over a wireless or wired computer or communications network, such as via a wide area network (WAN) such as the internet, to a remote user interface 206, where such information can be displayed and used by a neurologist to diagnose whether a seizure is present. A resulting diagnosis can be encrypted and transferred, at step 9F, over a wireless or wired computer or communications network, such as via a wide area network (WAN) such as the internet, to the remote server 704, and relayed at step 9H, to a hospital server 706. At step 9I, the diagnosis can be relayed over the hospital LAN to a computer terminal 708 located in the emergency department of the hospital. At step 10, in accordance with the diagnosis, the emergency department physician can request or provide appropriate treatment to the patient 202.

Figure 8:
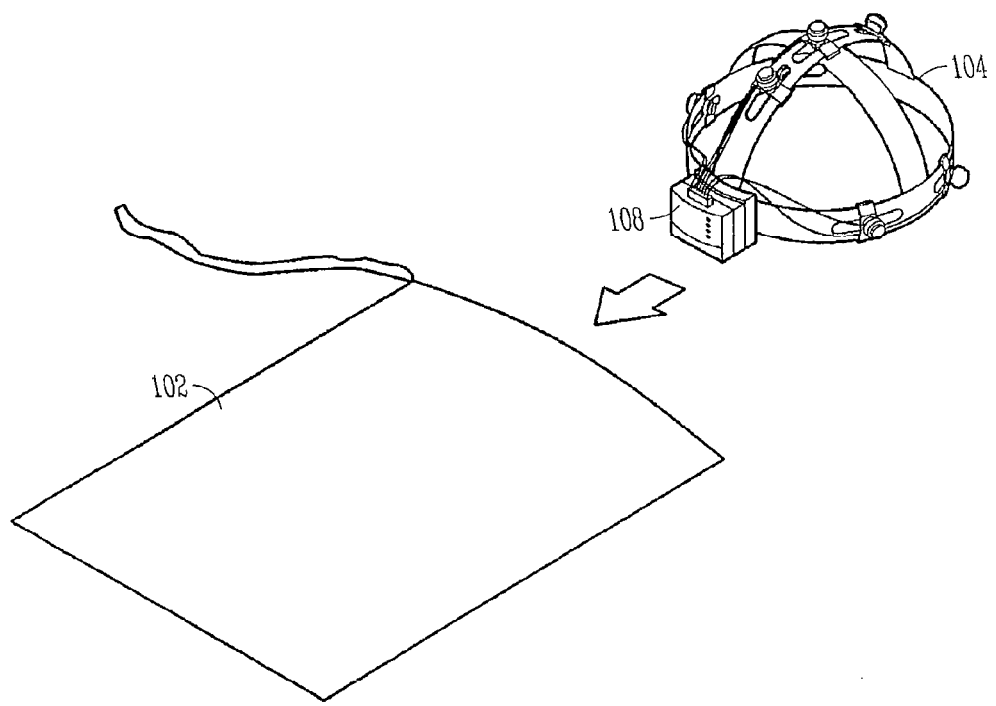

At step 11, shown in FIG. 8, the EEG recorder 108 and the headpiece 104 can be repackaged in the re-sealable EEG kit bag 102, such as for disposal or offsite refurbishment.

Example of Other e-NN Software Features

In addition to the automatic seizure diagnosis capability that can be provided at the remote server 704, the remote server 704 can be configured with further electronic neurologist network (e-NN) management software, which can include functionality for managing interactions between a network of remote neurologists and emergency departments or other users of the EEG kits. In an example, the e-NN can be provided at the UI 204. The e-NN can be conceptualized as extending from the UI out to the neurologists and back to the ED terminal. In an example, the e-NN management software can include capability for reading and encryption of EEG data and patient data, such as to assure patient privacy. The e-NN management software can include remote seizure diagnosis capability, such as described above, or by using third-party software. Using the automatic seizure diagnosis, a high probability diagnosis of non-seizure can be routed back to the emergency department, while a probable seizure can be routed to an appropriate remote neurologist such as for diagnosis or verification. The e-NN management software can prioritize routing to the network of remote neurologists, such as based upon information received from the emergency department or based upon results of the automatic diagnosis. The e-NN management software can route the diagnostic request to a primary neurologist, or to a primary neurologist and one or more secondary neurologists, such as for obtaining redundant diagnoses. The e-NN management software can also control routing of the resulting diagnoses back to the appropriate emergency department, such as where many emergency departments are concurrently being served. The e-NN management software can track the status of the diagnosis, such as whether an automatic or human diagnosis has been performed, and can assign a reliability factor to various different types of diagnosis. In an example, the e-NN management software can check one or more of the diagnoses against one or more known examples, such as to validate the diagnosis. In an example, the e-NN management software can resolve conflicts between multiple different diagnoses, such as by using a rule-based or other schema. In an example, the e-NN management software can evaluate and document neurologist performance, automatic diagnosis performance, or both.

Examples of Motion Artifact Management

Introduction to EEG Artifacts

The present inventors have recognized, among other things, that artifact rejection can play an important role in the interpretation or analysis of biomedical signals such as EEG signals. Signal artifacts, if not filtered or managed properly, can degrade the signal's quality or decrease or eliminate its usefulness. In particular, electroencephalographic signals (EEG) can suffer from a large number of artifacts that can originate from physiological or extraphysiological factors.

As described above, an EEG can record the brain's electrical activity, such as by using multiple electrodes placed on the patient's scalp. EEG can be a useful diagnostic tool for epilepsy because epilepsy's symptoms can appear as an abnormal pattern in the EEG signals. EEG signals can carry information about the brain's electrical activity that can be useful to EEG reviewers or interpreters, e.g., neurologists or epileptologists. But EEG signals can be influenced by a large number of other factors. For example the electrical activity of muscles in an EEG signal can be referred to as an Electromyogram (EMG) artifact. EMG artifacts can appear as a result of chewing or other motor activities. There can also be eye movement artifacts, such as can be associated with the electrical polarization of the eyeballs. EEG artifacts can also be caused by cardiac activity, which can be referred to as electrocardiogram (EKG or ECG) artifacts.

Artifacts in an EEG signal can resemble epileptic discharges, such as ictal or inter-ictal waveforms. The present inventors have recognized, among other things, that EEG interpreters need to clearly distinguish the EEG resulting from the brain's activity from artifacts arising from other sources. This can at times be difficult because the EEG from the brain's normal and abnormal electrical activity can occur in diverse patterns and can vary widely among individuals.

As a way of managing this problem, the present inventors have recognized, among other things, that one or more additional signals can be concurrently measured together with the scalp EEG and supplied to the EEG interpreters. For example, electrodes placed near the eyes (which can be denoted A1, A2 or "eye-leads") can carry information about eye movements. In addition, one or more EKG electrodes, such as at the chest, can show the heart's activity. When the EEG interpreter is faced with an ambiguity regarding the source of a feature or waveform of the EEG signal, the interpreter can view the scalp and non-scalp signals in parallel in order to help in interpreting the EEG signal and reaching a decision, such as to resolve the ambiguity. For example, if a small, sharp waveform on the scalp is repetitively occurring at the same times as the beats in the EKG, it can be concluded with reasonable certainty that such artifacts are not originating from the brain.

Electrode Motion Artifacts

An extraphysiological artifact that can be encountered in EEG interpretation is an electrode movement artifact, or electrode "pop." If an electrode moves relative to the scalp, its impedance can be abruptly affected, and this can cause various transients to appear in the EEG signal. Due to the sensitivity of an EEG signal amplifier circuit, even small impedance changes can result in large deviations in EEG signal amplitude. These electrode movement artifacts can be caused by very small physical movements (e.g., <1 mm). Movement of the patient's head can cause an electrode to move under its own inertia relative to the scalp if it is not securely attached. In another example, an object such as a pillow touching the patient's head can push an electrode and cause movement of that electrode relative to the scalp. In some cases, such movements appear on the EEG signal as movement artifacts that can mimic the waveforms generated by the brain's intrinsic dynamics and can resemble signals of interest and importance to the EEG reviewer.

In an EEG recording session for a walk-in patient, or in the epilepsy monitoring unit (EMU) in a neurology department of a hospital facility, the technicians or nurses who prepare and execute EEG recordings can implement a number of measures to eliminate electrode movement artifacts. These measures can include taking great care to ensure that the patient move as little as possible during the EEG recording, that no nearby objects in the patient's environment apply physical pressure to the electrode locations on the head, and that the electrodes are tightly attached to the scalp and are protectively wrapped by bandages applied to the entire head.

But these measures can be difficult or impossible to implement in an unconventional setting, such as in the emergency department (ED) or in an intensive care unit (ICU). In such unconventional settings the patient can be simultaneously undergoing examination, treatment, or transportation in parallel with the EEG recording. In such a chaotic or fast-moving environment, EEG electrodes can easily generate motion artifacts.

Even using rules of thumb or general advice intended to aid an EEG interpreter in rejecting electrode motion artifacts, the present inventors believe that no widely accepted method exists for reliably managing EEG electrode motion artifacts in the methodical manner of handling eye movement, EMG, and EKG artifacts.

Examples of Handling Motion Artifacts

The present inventors have recognized, among other things, that it can be helpful to provide the EEG interpreter (human or automated) with one or more signals indicative of electrode motion, which can then be used to reject such electrode motion artifacts in the EEG signal. In an example, such an electrode motion signal can be generated using an output from a miniature accelerometer that can be attached to an EEG electrode and, in a more particular example, using a combination of accelerometer outputs from respective accelerometers that can be individually attached to various corresponding EEG electrodes.

The present inventors have recognized, among other things, that proper EEG signal interpretation can benefit from distinguishing when a motion artifact is due to motion of an electrode relative to the scalp, as opposed to when the motion artifact is due to a global head or body movement. This is because the former (electrode movement relative to the scalp) causes impedance changes and, therefore, EEG motion artifacts, while the latter (electrode movement due to global head or body movement) does not cause impedance changes and, therefore, does not result in EEG motion artifact.

When the patient's head translates or rotates, electrodes will experience acceleration. However, for such global head or body movement, the electrodes will not move relative to the scalp, unless they have large enough inertia (unlike EEG electrodes) or are embedded and fixed in a rigid head piece with sufficient inertia (unlike EEG recordings), or the movements are sufficiently abrupt (unlike typical movements of a patient's head). Hence, under general conditions, the set of electrodes will move collectively as a rigid body and their relative distances from each other will remain constant. On the other hand, if only a particular electrode is subjected to a force, that particular electrode will move relative to the scalp and, therefore, the distance between that electrode and the other electrodes will also change. Therefore, the motion of an electrode relative to the scalp can therefore be reliably detected by monitoring the relative distances among electrodes. In an example, it is sufficient to monitor the distance of each electrode relative to a single reference position. This can be achieved by using signals from acceleration sensors attached to respective electrodes, such as described below.

In an example, each EEG electrode can be equipped with a sufficiently sensitive acceleration sensor, such as an accelerometer, attached thereto. In an example, such sensors can be associated with only a subset of the electrodes, if desired, and the present technique can also be applied to such a subset. In an example, each acceleration sensor can be capable of supplying signals proportional to the three spatial components of the acceleration vector experienced by the corresponding electrode. The acceleration signals can be input to the EEG recorder 108 and stored in its memory, such as along with the EEG signals measured by the electrodes. The acceleration of an electrode k at time t can be denoted as $a_k(t)$. The acceleration can be shown in bold in order to indicate that it can be a vector quantity, with three components corresponding to the three spatial directions.

In an example, it can be assumed that the accelerometers' axes are oriented in the same directions. In an example, this can be achieved by physically orienting them as such. In an example, the accelerometers need not be so physically oriented, and the technique described herein can be modified to transform the accelerations to a common basis.

Without loss of generality, the value 0 can be assigned to the initial position and velocities of all the electrodes: $x_k(0) = v_k(0) = 0, k=0, 1, 2, \ldots, N$. Kinematics then indicates that the positions, $x_k(t)$, and velocities, $v_k(t)$, at subsequent times can be given by $$x_k(t) = \int dt' v_k(t')$$

$$v_k(t) = \int dt' a_k(t').$$

In a discrete-time example, such as in which the accelerations are sampled at time intervals of size $\Delta t$, the position and velocity of electrode k at time $t_n$ can be found by the following approximate updating technique:

$x_k(t_n) = x_k(t_{n-1}) + \Delta t v_k(t)$ $v_k(t_n) = v_k(t_{n-1}) + \Delta t a_k(t).$ This technique requires that only the previous time step's positions and velocities be retained in order to calculate those of the next time step from the current acceleration. The approximation becomes more accurate for smaller sampling intervals. The updating can be made even more accurate if more than one previous time step's values are retained in the memory and used in a higher order computation.

In an example, one of the electrodes can be designated as a reference electrode and can be arbitrarily represented by index k=0. In an example, it can be beneficial to choose as the reference an electrode that is centrally located relative to the other electrodes, but this is not necessary. In an example, at every time step, a processor circuit can be used to calculate the magnitude of the relative displacement vectors for each non-reference electrode from the formula:

$R_k(t_n) = |x_k(t_n) - x_0(t_n)|, k=1,2,\ldots,N,$ where $|\cdot|$ can denote the magnitude of a vector, and $R_k(t_n)$ can denote the distance between electrode k and the reference electrode at time $t_n$. Note that following our choice of initial conditions, $R_k(t_n)=0$ for an electrode k unless the position of this electrode changes relative to the reference, or relative to the scalp.

The motion signals indicative of electrode motion are proportional to the rates of change of $R_k(t_n)$; therefore one can define:

$M_k(t_n) = R_k(t_n) - R_k(t_{n-1}).$

The motion signal $M_k(t_n)$ will be non-zero only during a period in which electrode motion relative to the scalp occurs. If the reference electrode itself moves relative to the scalp, this is signaled by the condition that $M_k$ is non-zero for all non-reference electrodes k. The measured value of the motion signal can depend on the average amount of acceleration during the sampling interval.

In another example, only scalar linear accelerations $a_k(t)$ can be measured. Each acceleration can be measured along a randomly oriented direction. When the head motion is a translation, all accelerations will, in general, be non-zero. If the head motion is a rotation, most electrodes will experience accelerations—except those that are located along the axis of rotation. Hence, in general, the motion of an electrode k relative to the scalp can be predicted by the fact that only the $k^{th}$ acceleration is non-zero while no other electrode experiences acceleration. The motion signal can therefore be computed from:

$$M_k(t_n) = a_k(t_n), \text{ if } a_j(t_n) = 0 \text{ for all } j \neq k,$$

$$= 0, \text{ otherwise}$$

In order to help ensure that the signals are easily observable, even for brief motions, a moving window averaged (or other central tendency) version of $M_k$ can be more suitable, in an example.

In various examples, the electrode motion signals can be used to:

1) Display them as additional traces on a the EEG display. Then, the EEG interpreter can visually monitor the electrode motion signals, such as to visually determine whether any waveforms resembling EEG signal artifacts are actually associated with, and presumably resulting from, electrode motion.

2) Modify the display style or color of the EEG traces using information about the motion of one or more of the electrodes. In an example, the processor can use information from the electrode motion signals to control the display, such that the display can change the color of an EEG trace derived from an electrode if that electrode's motion signal exceeds a specified threshold value.

3) Build a derived signal as the sum of all electrode motion signals so that electrode motion of any non-reference electrode is indicated by a nonzero value of this signal and that of the reference electrode is indicated by a large nonzero value.

Examples of Handling Motion Artifacts

Figure 9:
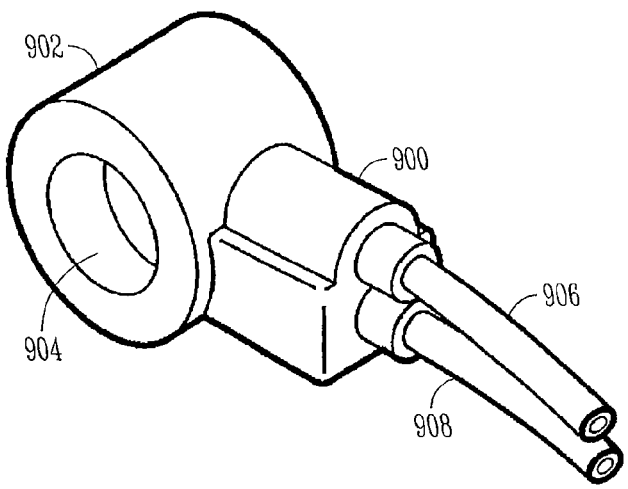
FIG. 9 is an example of an accelerometer-carrying housing for an electrode assembly, such as the electrode assembly.

FIG. 9 is an example of an accelerometer-carrying housing 900 for an electrode assembly, such as the electrode assembly 302. In an example, including such an accelerometer-carrying housing 900 at each of the electrode assemblies 302 that are associated with the headpiece 104, allows the determining of a local relative motion of a particular electrode assembly 302, which is deployed to be positioned at a particular location of the patient's scalp. Such local relative motion of a positioned electrode assembly 302 can cause a motion artifact that can be taken into account when interpreting an EEG signal from that particular electrode assembly 302, as described above.

In an example, the accelerometer-carrying housing 900 can include an integration or affixation mechanism such as a collar 902, which can provide a lumen 904, such that the collar 902 can be placed around at least a portion of an electrode assembly 302. Extending from the housing 900 can be a cable 906, which can include one or more electrically-insulated conductors, such as for carrying an EEG signal or one or more other signals (e.g., impedance, power, grounding, etc.) from the electrode assembly 302 to the EEG recorder assembly 108. Extending from the housing 900 can be a cable 908, which can include one or more electrically-insulated conductors, such as for carrying an accelerometer signal or one or more other signals (e.g., power, grounding, etc.) from an accelerometer in the housing 900 to the EEG recorder assembly 108. The cables 906 and 908 can be combined, in an example, or further separated into a greater number of cables.

Figure 10:
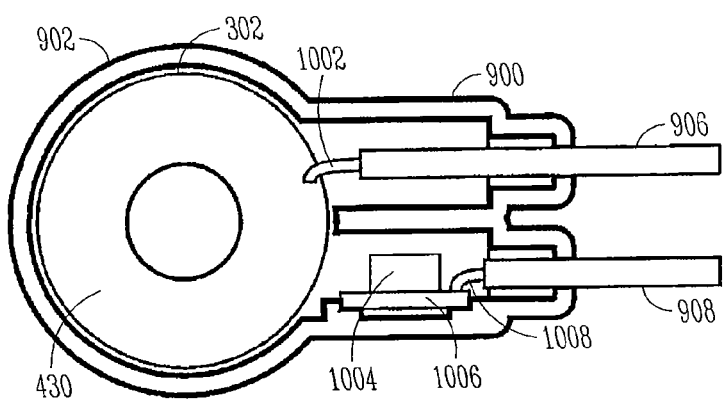
FIG. 10 is an another view of the housing, with the collar extending about an electrode assembly.

FIG. 10 is an another view of the housing 900, with the collar 902 extending about an electrode assembly 302. The cable 906 can include an electrically conductive wire 1002 that can be electrically connected to an electrically conductive flange 430 portion of the electrode assembly, such as to carry an EEG signal from the electrode assembly 302 to the EEG recorder assembly 108. The housing 900 can include an integrated circuit (IC) or other accelerometer 1004, which can be mounted to a printed circuit (PC) board 1006 (or hybrid circuit), which, in turn, can be mounted within the housing 900. The cable 908 can include an electrically conductive wire 1008 that can be electrically connected to the PC board 1006, which, in turn can be electrically connected via one or more traces or other electrically conductive connections to the accelerometer 1004. The electrically conductive wire 1008 can route an accelerometer signal from the housing 900 to the EEG recorder assembly 108. In this way, such an accelerometer signal can be recorded in time-synchronized concordance to the EEG signals, which can help in interpreting the EEG signals. For a multiple-axis accelerometer 1004, multiple electrically conductive wires 1008 can route separate accelerometer signals from the housing 900 to the EEG recorder assembly 108. In this way, such accelerometer signals can be recorded in time-synchronized concordance to the EEG signals, which can help in interpreting the EEG signals, such as to avoid erroneously interpreting a motion-artifact in the EEG signal as an actual neurological event.

Figure 11:
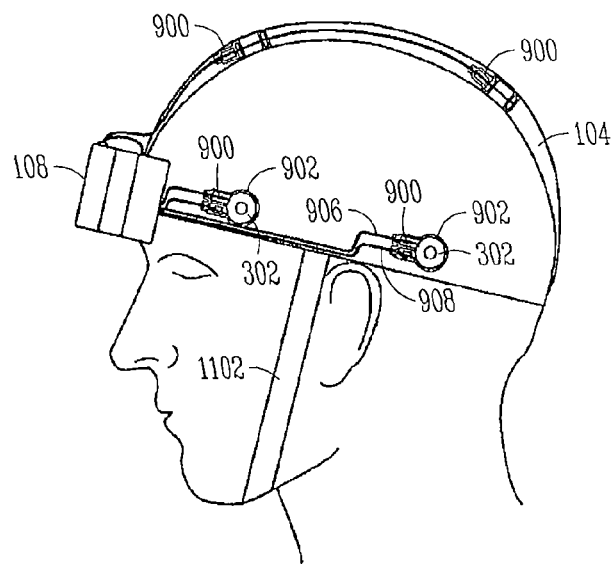
FIG. 11 shows an example of the headpiece in place on a patient's head, with the EEG recorder assembly mounted to the headpiece.

FIG. 11 shows an example of the headpiece 104 in place on a patient's head 202, with the EEG recorder assembly 108 mounted to the headpiece 104, which, in an example, can include an optional chin strap 1102. In this example, individual accelerometer-carrying housings 900 can be co-located with their respective electrode assemblies 302, such as by having respective collars 902 snugly encircling such respective electrode assemblies 302. The cables 906 and 908 from the individual accelerometer-carrying housings 900 can be routed, such as along a support member of the headpiece 104, to the EEG recorder assembly 108. This can allow each electrode assembly 302 to provide one or more EEG signals and one or more corresponding accelerometer signals from that particular electrode assembly 302 to the EEG recorder assembly 108, such as to help in manually or automatically interpreting an EEG signal from that particular electrode assembly 302.

Figure 12:
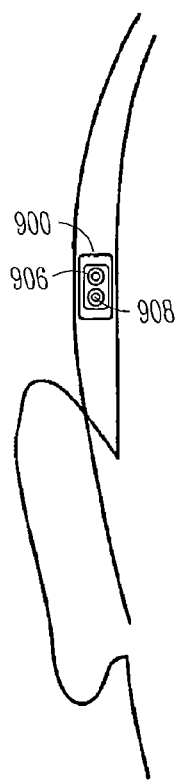
FIG. 12 shows another view (e.g., from a viewpoint facing the front of the patient) of a housing and cables.

FIG. 12 shows another view (e.g., from a viewpoint facing the front of the patient) of a housing 900 and cables 906 and 908.

Examples of Some Variations

Many variations in using the system 200 and the local user interface device 204 are possible. In an example, a small number of local user interface devices 204 with a large or unlimited supply of EEG kit bags 102 can be supplied to an emergency department, such as part of an initial emergency department setup for the present systems and methods. In another example, a single local user interface device can be provided with or within each EEG kit bag 102. In another example, a touch-screen or other display (e.g., a liquid crystal display (LCD)) can be integrated into the EEG recorder 108, such as for providing a user interface or for displaying EEG information or the like. In an example, since most emergency departments are connected to a local-area network, an existing local keyboard and networked computer terminal can be employed as the local user interface device 204. In another example, the local user interface device 204 is omitted, and the components in the EEG bag 102 shown in FIG. 1 can be used without a local user interface device 204 to acquire the EEG data. In such an example, the memory card 110 can be used to transfer the data to another device for diagnosis (e.g., by a neurologist or by an automatic process) or verification or documentation. In another example, the EEG recorder 108 can include electronics such as a digital signal processor (DSP) or other processor that can perform on-board analysis of EEG signal quality or automatic seizure diagnosis using the EEG signal information. In another example, the local user interface device 204 can be provided and can include a bar code scanner or other optical or other scanner, such as to input patient information that has previously been encoded or associated with such a bar code or the like.

Figure 13:
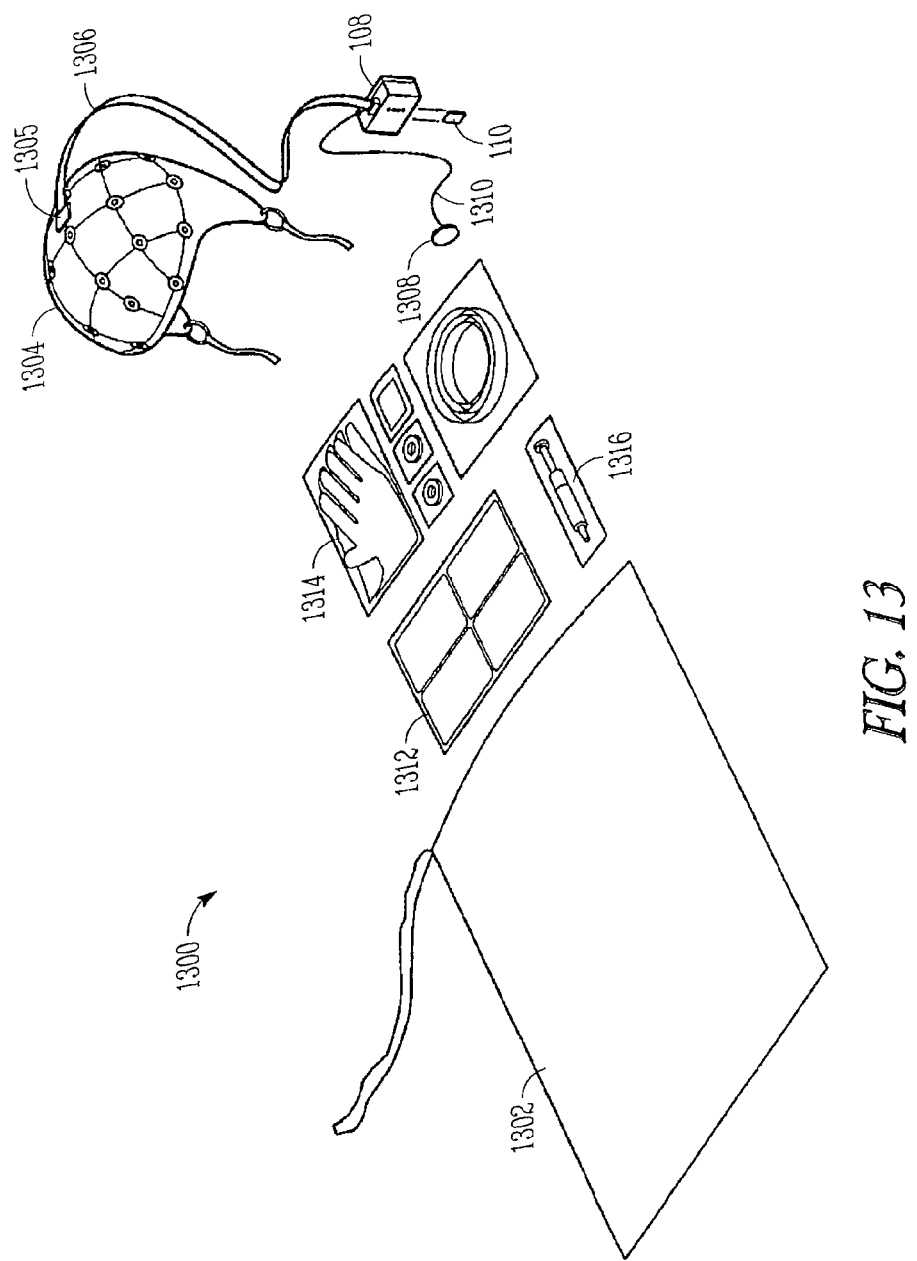
FIG. 13 shows another example of an EEG kit.

FIG. 13 shows another example of an EEG kit 1300. In an example, the EEG kit 1300 can include a internally-sterilized bag 1302 that includes a different headpiece 1304 from the headpiece 104 of FIG. 1. In an example, the different headpiece 1304 need not have the EEG recorder assembly 108 mounted to the headpiece 1304. Instead, the EEG recorder assembly 108 can be electrically connected to a connector 1305 on the headpiece 1304 such as by a length of multi-conductor ribbon cable 1306, although such an example may be more subject to ambient noise, such as can be coupled in through the cable 1306. In an example, a chest electrode 1308 or other body electrode can be electrically connected to the EEG recorder assembly 108, such as by an appropriate length (e.g., less than 50 cm, less than 40 cm, less than 30 cm, less than 20 cm, or less than 10 cm) of cable 1310. The chest electrode 1308 can be used to detect an ECG or EKG signal, such as from the subject's chest area, such as to be recorded by the EEG recorder assembly in time concordance with the recorded EEG signals. This can help in manually or automatically analyzing the EEG signals to determine whether a feature of the EEG signal represents an actual neurological event, or is merely a ECG signal artifact. The EEG kit 1300 can also include (e.g., packaged together in the bag 1302 or separately provided in or with the EEG kit 1300) instructions for use (IFUs) 1312, sterile gloves 1314, conductive fluid or saline (e.g., in a syringe or other container) 1316, and any or all other ancillary items for performing the ambulatory head-mounted scalp-worn EEG procedure, such as the user interface 204, optionally. In an example, the user interface 204 can be packaged together in the bag 1302. In an example, the user interface 204 can be packaged in the EEG kit 1300 package separately from the items in the bag 1302, such as where the bag 1302 and the user interface 204 are both packaged together in an overall package of the EEG kit 1300. In an example in which the user interface 204 is packaged separately, the bag 1302 can have dimensions of about 12 inches by 8 inches by 2 inches.

In an example, the headpiece 1304 can include an elastic spandex-type electrode cap, such as available from Electro-Cap International, Inc., of Eaton, Ohio (www.electro-cap.com). In an example, the headpiece 1304 can include a HydroCel Geodesic Sensor Net (HCGSN), such as available from Electrical Geodesics, Inc., of Eugene, Oreg. (www.egi.com/research-division-research-products/sensor-nets). In an example, the headpiece 1304 can include a STATNET™ or EZENET® EEG electrode system and harness, such as available from Hydrodot, Inc., of Westford, Mass. (www.hydrodot.net).

Figure 14:
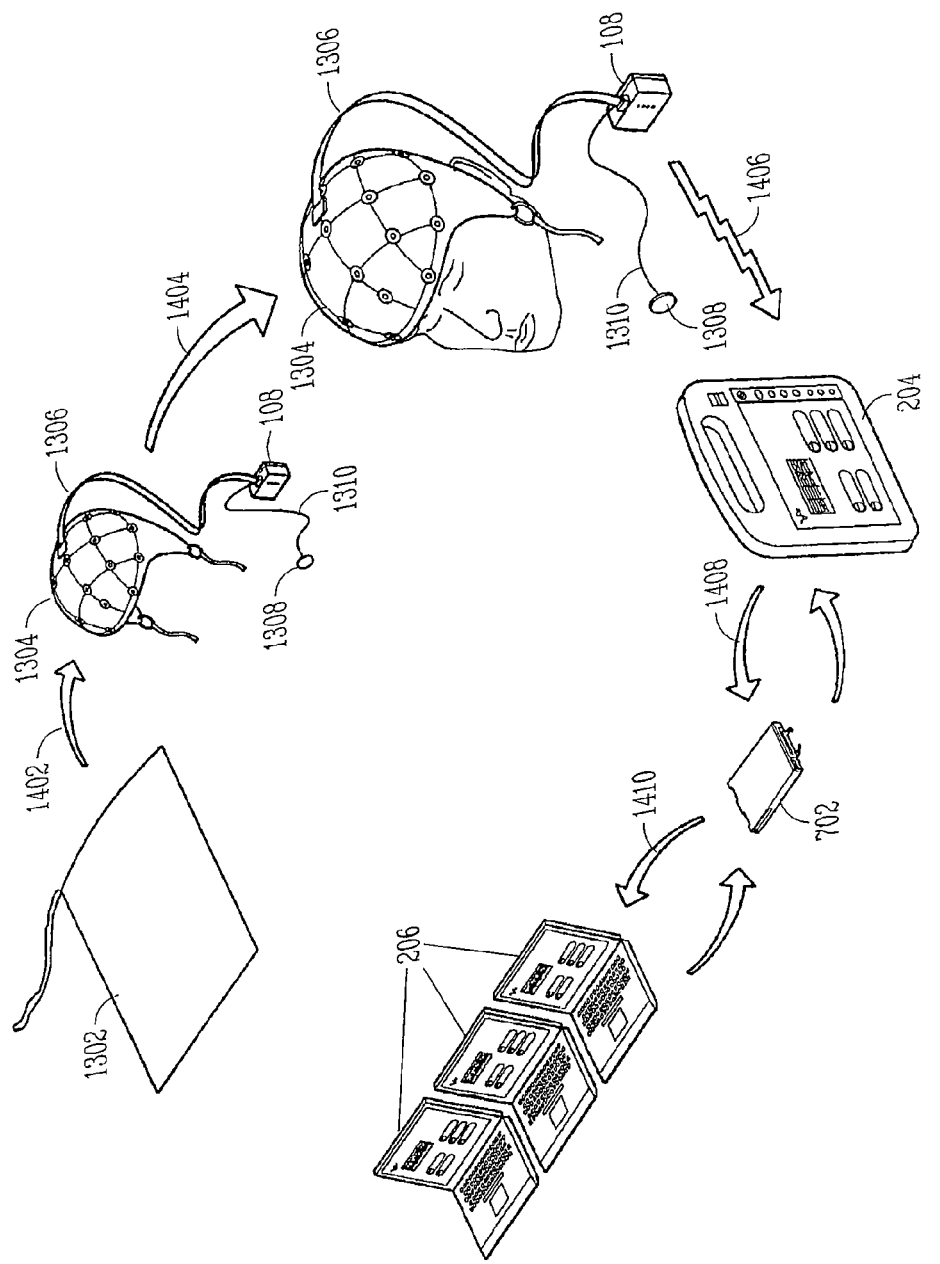
FIG. 14 shows an example in which the headpiece, EEG recorder, and chest electrode are removed from the bag, used for recording EEG or other signals, which can be communicated to an adjunct computing device, such as for display, triage, prioritization, or further manual or automatic analysis or diagnosis.

FIG. 14 shows an example in which, at 1402, the headpiece 1304, EEG recorder 108, and chest electrode 1308 are removed from the bag 1302. At 1404, the headpiece 1304 can be placed on the patient's head and connected to the EEG recorder 108, such as by using the ribbon cable 1306. The chest electrode 1308 can be placed on the patient's chest and connected to the EEG recorder, such as via the cable 1310. At 1406, EEG signals acquired and recorded by the EEG recorder 108, along with any corresponding local electrode motion signals, ECG signals, or other signals of interest, can be transferred to a local user interface 204, such as for display allowing manual human diagnosis, or for signal processing for automatic diagnosis of a seizure or other neurological condition. At 1408, such signals or information derived therefrom can be transferred to a remote data collection device 702, such as a computer or server or the like that can be located elsewhere within the hospital. At 1410, such signals or information derived therefrom can be transferred to the remote user interface device 206, such as for display or other use by a remote diagnosing neurologist or for automatic processing of the recorded EEG data or other data. Any such diagnosis can be communicated back to the local user interface, such as via the computer-network-enabled remote data collection device 702.

In an example, the automatic processing of the recorded EEG data or other data need not perform a final diagnosis of a neurological condition such as a seizure. Instead, the automatic processing of the recorded EEG data or other data can be used to perform an initial triage assessment of the neurological condition. This can be carried out, in an example, by a signal processor circuit, such as at the remote data collection device 702, which can collect data from several, or even many different patients who are located in the same facility, or who are located in different facilities. In an example, the initial triage assessment can be used to rank the severity of the neurological condition, such as for prioritizing the patient data of various patients for presentation for display to a diagnosing neurologist. In this way, those patients presenting with the most severe neurological conditions (e.g., according to the initial diagnosis made by the automatic signal processing of the recorded EEG data or other data) can be further diagnosed by a remote or local attending diagnosing neurologist or other caregiver before other patients presenting with less severe neurological conditions (e.g., as determined from the initial triage made by the automatic signal processing of the recorded EEG data or other data). In an example, the remote data collection device 702 can include signal processing to monitor or compare the performance of various diagnosing neurologists (e.g., accuracy, responsiveness/timeliness, etc.).

Figure 15:
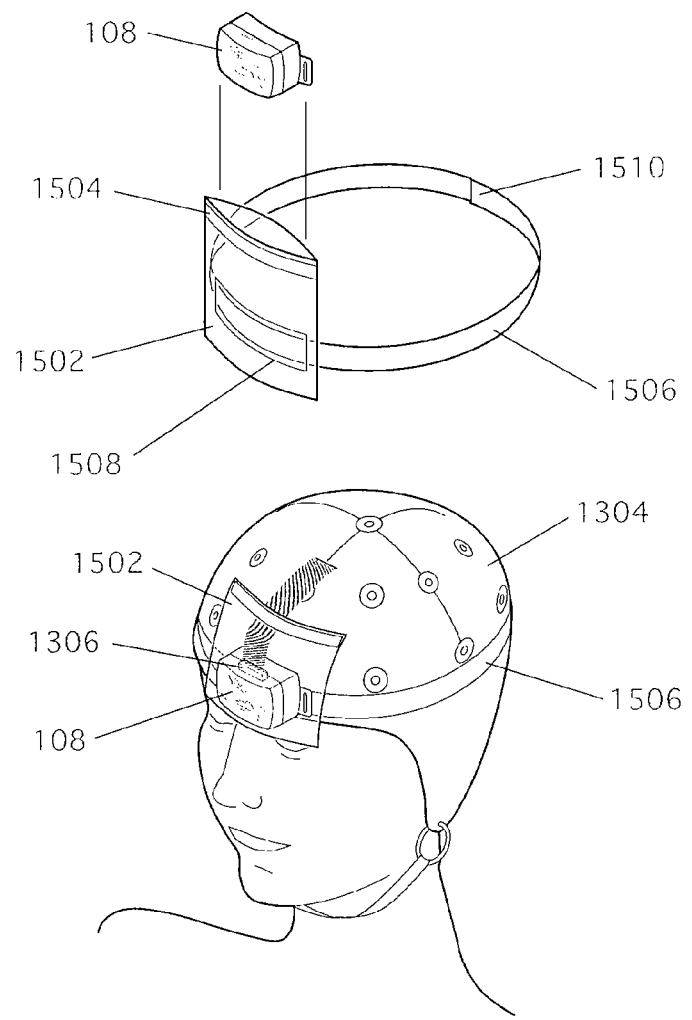
FIG. 15 shows an example of a single-use recorder pouch that can be included in the EEG kit.

FIG. 15 shows an example in which the EEG kit 1300 can include or be accompanied by a single-use cover or bag or pouch 1502, such as can be packaged within the bag 1302. The pouch 1502 can be sized and shaped to carry the recorder 108 therewithin, such as placed therewithin by the end-user or by the manufacturer of the EEG kit 1300. The single-use pouch 1502 can help protect the multiple-use (or other) recorder from being contacted by blood, sweat, or other fluids that may be present in an ED or other environment, such as by being made from a fluid-impervious material, such as polyethylene, or the like. The EEG recorder assembly 108 in the pouch 1502 can be electrically connected to a connector 1305 on the headpiece 1304, such as by a multi-conductor cable, such as the ribbon cable 1306. An single-use transfer adhesive seal 1504 can close and seal off the pouch 1502 with the ribbon cable 1306 passing from the sealed interior of the pouch 1502 to the exterior of the pouch 1502. A peel-away liner can protect the adhesive seal 1504 from performing such closing and sealing until such closing and sealing is desired, at which time the peel-away liner can be removed, such as to expose the adhesive of the adhesive seal 1504. Sealing of the pouch 1502 can be performed by either the end-user or by the manufacturer, as desired. The adhesive material can be selected to provide desired adhesion characteristics, such as to inhibit or prevent re-sealing after unsealing, or to provide enough adhesive force (e.g., relative to the tear strength of the pouch 1502), such that the adhesive seal cannot be unsealed without tearing or otherwise rendering the pouch 1502 unsuitable for a second or subsequent use.

The pouch 1502, with the carried recorder 108, can be mounted to the headpiece 1304 or the subject's head, such as to permit ambulatory EEG recording or data transmission. In an example, this can include mounting the pouch 1502 to an elastic or other flexible headband 1506, which, in turn, can be worn on or about the subject's head such as over the headpiece 1304. In an example, an exterior surface of the pouch 1502 can include a sleeve 1508 through which the headband 1506 can be passed, such as to mount the pouch 1502 to the headband 1506. This can also permit the pouch 1502 to be slid along the headband 1506, such as to position or reposition the pouch 1502 to a desired location on the subject's head, which can provide convenience and flexibility. However, the pouch 1502 can be affixed to the headband 1506—or directly to the headpiece 1304—using another affixation technique that can preserve the fluid-impervious nature of the pouch 1502, such as an adhesive strip (e.g., with a peel-away liner) or the like. In an example, the headband 1502 can include one or more length-adjustment features to allow length adjustment of the headband 1502, such as to accommodate different head sizes—in addition to as an alternative to any stretching that can optionally be provided by the headband 1506. In an example, the length-adjustment features can include VELCRO hook-and-loop or other attachment tabs 1510 that can be positioned at desired locations along the headband 1506, such as to permit length adjustment of the headband 1506, e.g., by +/-3 inches, which can have a nominal length that is sized to fit most adult head sizes. The headband 1506 and the pouch 1502 can together be referred to as a "One-Use Cover" (OUC). The headband 1506 and the pouch 1502 can be packaged together in the bag 1302 or other package of the EEG kit 1300, either pre-attached to each other with the recorder 108 already sealed in the pouch 1502 by the manufacturer, or separately, such that the end-user can place the recorder 108 in the pouch 1502 and slip the headband 1506 through the sleeve 1508.

To recap, the OUC can help protect the recorder 108 and its enclosed electronics from being splashed with fluids, such as can be associated with the ED. These fluids could potentially short-circuit the electronics or damage or contaminate the recorder 108, which, in turn, could delay a possibly time-sensitive diagnostic test. If the recorder 108 were to come into direct contact with the patient during an examination, it would require a thorough cleaning after each use. An inexpensive solution can include using a plastic bag or sterile drape, such as the pouch 1502, which can be placed over the recorder 108, used once, and then disposed of. This method can keep the reusable recorder 108 equipment on-line by significantly reducing the need for costly or time-consuming cleaning procedures. The OUC can provide a protective nesting pouch 1502 for the recorder 108 and can relieve the strain on the ribbon cable 1306 connector connecting the electrode cap 1304 to the recorder 108.

ADDITIONAL NOTES

It is advantageous to rigidly attach the EEG monitoring electronics directly to the electrodes, such as to decrease or minimize noise, however this is often impractical. However, the EEG recorder 108 can be made sufficiently small to be attached directly to the subject's head, such as described above. If head-mounting proves impractical, the EEG recorder 108 can be mounted on the patient's upper arm, or elsewhere on the patient's body, such as in a location that can minimize the distance between the electrode-scalp interface and the EEG recorder 108.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like. The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. An apparatus comprising an electroencephalographic (EEG) monitoring kit comprising a kit package comprising:
    an EEG recording module, configured to be worn on a head of a patient, the EEG recording module comprising a memory configured for recording a plurality of EEG signals from the patient;
    a headpiece, sized and shaped to be worn on the head of the patient, the headpiece comprising a plurality of non-surgically implanted scalp-wearable electrode assemblies that are configured to be electrically connected to the EEG recording module;
    an electrical connector cable, having a length that is less than 50 centimeters, the cable configured to couple the EEG recording module to the headpiece, when both the EEG recording module and the headpiece are worn on the head of the patient, to communicate the EEG signals from the electrode assemblies to the EEG recording module; and
    a fluid-impervious single-use cover, configured to be directly or indirectly mounted to the headpiece or to the head of the patient, the cover sized or shaped to carry the EEG recording module within the cover and configured to permit the cable to extend Out from the cover to the headpiece, wherein the cover comprises a flexible plastic pouch comprising an adhesive seal, configured to seal the EEG recording module within the pouch with the cable extending out from the pouch, and wherein the pouch is configured with a tear strength that is less than an adhesion strength of the adhesive seal such that opening the sealed pouch to remove the EEG recording module from the pouch requires tearing of the pouch and thereby renders the pouch unsuitable for subsequent use with the EEG recording module.

2. The apparatus of claim 1, wherein the cover comprises a pouch that comprises a mount, configured to directly or indirectly mount the pouch to the headpiece or the head of the patient.

3. The apparatus of claim 2, wherein the EEG kit package comprises a headband, sized or shaped to be worn directly or indirectly about the head of the patient, and wherein the pouch comprises the mount including a sleeve that is sized or shaped to pass the headband through the sleeve for mounting the pouch for being worn directly or indirectly about the head of the patient.

4. The apparatus of claim 3, wherein the headband includes an elastic portion to allow stretching of the headband.

5. The apparatus of claim 4, wherein the headband further includes an additional length adjustment feature beyond the stretching.

6. The apparatus of claim 5, wherein the additional length adjustment feature includes a series of spaced-apart affixation tabs located on the headband.

7. The apparatus of claim 1, wherein the headpiece comprises a head-receiving configuration of support members, the configuration of support members carrying a plurality of electrode assemblies that are electrically connected to the EEG recording module and that respectively ride along a respective position adjustment track so as to be capable of being individually relocated by a user from a first location on the patient's head to a different second location on the patient's head while the headpiece is in place on the patient's head.

8. The apparatus of claim 1, wherein at least one of the electrode assemblies comprises a plunger, configured to allow user-adjustment of an electrode toward a scalp of the patient, and wherein the plunger is configured to rupture a seal to allow user-actuated release of an at least somewhat flowable conductive substance toward a skin-electrode interface to assist in obtaining electrical conduction at the skin-electrode interface.

9. The apparatus of claim 1, wherein each one of the electrode assemblies comprises a respective accelerometer attached to that one of the electrode assemblies and wherein the EEG recording module further comprises a signal processor circuit coupled to the accelerometers, the signal processor configured to permit detecting relative movement of that particular one of the electrode assemblies beyond global motion of the patient's head or body.

10. The apparatus of claim 1, wherein the EEG recording module comprises an impedance test circuit, configured to measure a skin-electrode impedance of an individual electrode configured to provide an EEG signal.

11. The apparatus of claim 1, comprising a user interface, configured to be capable of being communicatively coupled to the memory of the EEG recording module and configured to receive information from the recorded plurality of EEG signals, and wherein the user interface includes or is configured to be coupled to a camera to obtain images of the patient to be stored in concordance with the plurality of EEG signals.

12. The apparatus of claim 1, wherein the EEG recording module includes a non-EEG physiological sensor interface configured to receive at least one non-EEG physiological signal, and wherein the EEG recording module is configured to record the non-EEG physiological signal in concordance with the plurality of EEG signals.

13. The apparatus of claim 1, wherein the headpiece includes a local position monitor configured to monitor the position of at least one of the electrode assemblies and to provide an indication of the position of the monitored at least one electrode assembly to the memory of the EEG recording module for recording.

14. The apparatus of claim 1, further comprising an adjunct computing device, capable of being communicatively coupled to the memory of the EEG recording module and configured to receive information from the recorded plurality of EEG signals, and wherein the adjunct computing device includes or is configured to be coupled to processor configured to perform seizure detection using information from the recorded plurality of EEG signals.

15. The apparatus of claim 14, wherein the adjunct computing device is configured to be communicatively coupled to a plurality of EEG recording modules.

16. The apparatus of claim 15, wherein the adjunct computing device includes or is coupled to a memory circuit including instructions that, when performed by a processor circuit of the adjunct computing device, analyzes EEG signals from the plurality of EEG recording modules associated with different patients to permit prioritizing patients for further attention.

17. The apparatus of claim 14, wherein the adjunct computing device includes or is coupled to a memory circuit that is configured to record a measure of performance of a plurality of human reviewers.

18. An apparatus comprising an electroencephalographic (EEG) monitoring kit comprising a kit package comprising:
an EEG recording module, configured to be worn on a head of a patient, the EEG recording module comprising a memory configured for recording a plurality of EEG signals from the patient;
a headpiece, sized and shaped to be worn on the head of the patient, the headpiece comprising a plurality of non-surgically implanted scalp-wearable electrode assemblies that are configured to be electrically connected to the EEG recording module;
an electrical connector cable, having a length that is less than 50 centimeters, the cable configured to couple the EEG recording module to the headpiece, when both are worn on the head of the patient, to communicate the EEG signals from the electrode assemblies to the EEG recording module;
a fluid-impervious single-use cover, configured to be directly or indirectly mounted to the headpiece or to the head of the patient, the cover sized or shaped to carry the EEG recording module within the cover and configured to permit the cable to extend out from the cover to the headpiece, wherein the cover comprises a flexible plastic pouch comprising an adhesive seal, configured to seal the EEG recording module within the pouch with the cable extending out from the pouch, wherein the pouch is configured with a tear strength that is less than an adhesion strength of the adhesive seal such that opening the sealed pouch to remove the EEG recording module from the pouch requires tearing of the pouch and thereby renders the pouch unsuitable for subsequent use with the EEG recording module, wherein the pouch comprises a mounting sleeve, configured to directly or indirectly mount the pouch to the headpiece or the head of the patient; and
a headband, including a stretchable elastic portion, the headband sized or shaped to be worn directly or indirectly about the head of the patient, and wherein the mounting sleeve of the pouch is sized or shaped to pass the headband through the sleeve for mounting the pouch for being worn directly or indirectly about the head of the patient.

19. The apparatus of claim 18, wherein each one of the electrode assemblies comprises a respective accelerometer attached to that one of the electrode assemblies and wherein the EEG recording module further comprises a signal processor circuit coupled to the accelerometers, the signal processor configured to permit detecting relative movement of that particular one of the electrode assemblies beyond global motion of the patient's head or body; and
wherein the EEG recording module comprises an impedance test circuit, configured to measure a skin-electrode impedance of an individual electrode configured to provide an EEG signal.

20. The apparatus of claim 1, wherein the flexible plastic pouch comprises a polyethylene bag.

21. The apparatus of claim 1, wherein the flexible plastic pouch comprises a single-use transfer adhesive seal.

22. The apparatus of claim 21, wherein the single-use transfer adhesive seal includes a peel-away liner configured to be removed by an end-user to expose the adhesive of the adhesive seal.

23. The apparatus of claim 22, wherein the adhesive material includes an adhesion characteristic that prevents re-sealing after unsealing.

24. The apparatus of claim 1, wherein the pouch is flexible enough to allow insertion of the electronics unit into the pouch through an open end of the pouch that is capable of then being closed and sealed using the adhesive seal.

* * * * *